United States Patent
Chen et al.

(10) Patent No.: US 7,390,760 B1
(45) Date of Patent: Jun. 24, 2008

(54) COMPOSITE NANOFIBER MATERIALS AND METHODS FOR MAKING SAME

(75) Inventors: Fung-jou Chen, Appleton, WI (US); Lei Huang, Duluth, GA (US); Jeffrey D. Lindsay, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 115 days.

(21) Appl. No.: 10/979,301

(22) Filed: Nov. 2, 2004

(51) Int. Cl.
*D04H 1/00* (2006.01)
*D04H 1/46* (2006.01)
*B32B 5/26* (2006.01)

(52) U.S. Cl. .................. 442/341; 442/340; 442/344; 442/392; 442/403

(58) Field of Classification Search .................. 442/340, 442/341, 344, 345, 346, 381, 392, 402, 403; 428/218
See application file for complete search history.

(56) References Cited

U.S. PATENT DOCUMENTS

| | | | |
|---|---|---|---|
| 808,433 | A | 12/1905 | Cartledge |
| 3,125,093 | A | 3/1964 | Hutchins |
| 3,490,115 | A | 1/1970 | Owens et al. |
| 3,940,115 | A | 2/1976 | Zipperer |
| 4,230,650 | A | 10/1980 | Guignard |
| 4,699,133 | A | 10/1987 | Schafer et al. |
| 4,820,296 | A | 4/1989 | Masliyah |
| 5,151,092 | A | 9/1992 | Buell et al. |
| 5,238,733 | A | 8/1993 | Joseph et al. |
| 5,609,727 | A | 3/1997 | Hansen et al. |
| 5,624,423 | A | 4/1997 | Anjur et al. |
| 4,043,331 | A | 8/1997 | Martin et al. |

(Continued)

FOREIGN PATENT DOCUMENTS

EP 0361842 A2 4/1990

(Continued)

OTHER PUBLICATIONS

ALPHAGALILEO.ORG, "Lotus effect shakes off dirt", http://www.sciencenet.org.uk/news/2002/1102/lotus.html, (2002), 1 page.

(Continued)

*Primary Examiner*—Jenna-Leigh Johnson
(74) *Attorney, Agent, or Firm*—Nancy M. Klembus; Alyssa Dudkowski

(57) ABSTRACT

A composite material comprising a plurality of nanofibers intertwined with a plurality of coarse fibers to form one or more layers is provided. The nanofibers can be any suitable type of nanofiber, including electrospun fibers. A composite material comprising a plurality of electrospun fibers intertwined with a plurality of coarse fibers to form a single layer is also provided. A composite material comprising a plurality of electrospun fibers combined with a plurality of coarse fibers to form a plurality of layers, i.e., a multi-layer material, is also provided. In some embodiments, gradients in one or more directions are produced. Embodiments of the invention also provide processes for producing the composite nanofiber material. The materials are useful for any type of disposable garment, wipe, hospital garment, face mask, sterile wrap, air filter, water filter and so forth. Materials described herein can provide strong and varying surface effects, such as wicking. In one embodiment, hydrophobic fibers have a sufficiently small diameter to create a lotus effect.

50 Claims, 8 Drawing Sheets

U.S. PATENT DOCUMENTS

| | | | |
|---|---|---|---|
| 5,683,794 | A | 11/1997 | Wadsworth et al. |
| 5,795,584 | A | 8/1998 | Totakura et al. |
| 5,935,370 | A | 8/1999 | Weimer et al. |
| 6,024,813 | A * | 2/2000 | Groeger et al. ............. 156/62.8 |
| 6,033,684 | A | 3/2000 | Norcia |
| 6,106,913 | A | 8/2000 | Scardino et al. |
| 6,114,024 | A | 9/2000 | Forte |
| 6,315,806 | B1 * | 11/2001 | Torobin et al. ................ 55/522 |
| 6,382,526 | B1 | 5/2002 | Reneker et al. |
| 6,395,046 | B1 | 5/2002 | Emig et al. |
| 6,488,731 | B2 | 12/2002 | Schultheiss et al. |
| 6,492,574 | B1 | 12/2002 | Chen |
| 6,520,425 | B1 | 2/2003 | Reneker |
| 6,573,419 | B2 | 6/2003 | Naimer |
| 6,617,490 | B1 | 9/2003 | Chen et al. |
| 6,660,363 | B1 | 12/2003 | Barthlott .................... 428/141 |
| 6,673,136 | B2 | 1/2004 | Gillingham et al. |
| 6,685,956 | B2 | 2/2004 | Chu et al. |
| 6,689,374 | B2 | 2/2004 | Chu et al. |
| 6,706,086 | B2 | 3/2004 | Emig et al. |
| 6,713,011 | B2 | 3/2004 | Chu et al. |
| 6,743,273 | B2 | 6/2004 | Chung et al. |
| 6,753,454 | B1 | 6/2004 | Smith et al. |
| 7,018,188 | B2 | 3/2006 | James et al. |
| 7,112,621 | B2 | 9/2006 | Rohrbaugh et al. |
| 7,134,857 | B2 | 11/2006 | Andrady et al. |
| 2001/0045547 | A1 | 11/2001 | Senecal et al. |
| 2002/0150724 | A1 | 10/2002 | Nun et al. ................... 428/143 |
| 2002/0175449 | A1 | 11/2002 | Chu et al. |
| 2003/0026985 | A1 | 2/2003 | Greiner et al. |
| 2003/0069369 | A1 | 4/2003 | Belenkaya et al. |
| 2003/0100944 | A1 | 5/2003 | Laksin et al. |
| 2003/0121380 | A1 | 7/2003 | Cowell et al. |
| 2003/0228350 | A1 | 12/2003 | Chu et al. |
| 2004/0054406 | A1 | 3/2004 | Dubson et al. |
| 2004/0092185 | A1 | 5/2004 | Grafe et al. |
| 2004/0096533 | A1 | 5/2004 | Dubson et al. |
| 2004/0097895 | A1 | 5/2004 | Busam et al. |
| 2004/0106343 | A1 | 6/2004 | Senecal et al. |
| 2004/0116028 | A1 | 6/2004 | Bryner |
| 2004/0158214 | A1 | 8/2004 | Ponomarenko et al. |
| 2004/0203306 | A1 | 10/2004 | Grafe et al. |
| 2004/0266300 | A1 | 12/2004 | Isele et al. |
| 2005/0026526 | A1 * | 2/2005 | Verdegan et al. ............ 442/340 |
| 2005/0033253 | A1 | 2/2005 | Fuchs et al. |
| 2005/0048274 | A1 | 3/2005 | Rabolt et al. |
| 2005/0053784 | A1 | 3/2005 | Wood et al. |
| 2005/0164584 | A1 | 7/2005 | Baratian et al. |
| 2005/0253305 | A1 | 11/2005 | Kim et al. |
| 2005/0287239 | A1 | 12/2005 | Joo et al. |
| 2006/0094320 | A1 | 5/2006 | Chen et al. |

FOREIGN PATENT DOCUMENTS

| | | |
|---|---|---|
| EP | 1283283 A1 | 2/2003 |
| WO | WO-98/03267 A1 | 1/1998 |
| WO | WO-01/27365 A1 | 4/2001 |
| WO | WO-01/97731 A2 | 12/2001 |
| WO | WO-02/20668 A2 | 3/2002 |
| WO | WO-03/062510 A1 | 7/2003 |
| WO | WO-03086234 A2 | 10/2003 |
| WO | WO-2005/040495 A1 | 5/2005 |
| WO | WO-2005073441 A1 | 8/2005 |
| WO | WO-2005/103354 A1 | 11/2005 |
| WO | WO-2006/049663 A1 | 5/2006 |
| WO | WO-2006/049664 A1 | 5/2006 |

OTHER PUBLICATIONS

Cornell University, "Ellectrospinning celulose waste into fiber", *Science Daily*, http://www.sciencedaily.com/releases/2003/09/030911072323.htm, (Sep. 11, 2003),2 pages.

Dai, Hongqin, et al., "A novel method for preparing ultra-fine alumina-borate oxide fibres via an electrospinning technique", *Nanotechnology*, 13(5), (Oct. 2002),674-677.

Dersch, M, "Electrospinning of Nanostructured Composite Fibers", *New Frontiers in Fiber Science, Spring Meeting*, (May 23-25, 2001).

Diaz-de Leon, M J., "Electrospinning Nanofibers of Polyaniline and Polyaniline / (Polystyrene and Polyethylene Oxide) Blends", *Proceedings of The National Conference on Undergraduate Research (NCUR) 2001, University of Kentucky*, (Mar. 15-17, 2001).

Gibson, Phillip, "Changes in Porosity and Transport Properties of Microporous Elastomeric Electrospun Nonwoven Membranes Under Biaxial Strain Conditions", *New Frontiers in Fiber Science, Spring Meeting*, (May 23-25, 2001).

Gibson, P. W., et al., "Electrospun fiber mats: transport properties", *AIChE Journal*, 45(1), (Jan. 1999 (45)1), 190-95.

Hagewood, J, "Ultra Microfibers: Beyond Evolution", *International Fiber Journal*, http://www.ifj.com/issue/october98/story8.html, (Oct. 1998),4 pages.

Hou, H, "Preparation of oriented nano- and mesotubes by electrospun template fibers (TUFT-process)", *New Frontiers in Fiber Science, Spring Meeting*, (May 23-25, 2001).

Jacoby, M., "Hollow nanofibers in a single step", *Chemical and Engineering News*, (82)17, (Apr. 26, 2004),6.

Jin, Hyoung-Joon, "Electrospinning Bombyx Mori Silk with Poly-(ethylene oxide)", *Biomacromolecules*, 3(6), (Nov. 2002), 1233-1239.

Lang, S., "Researchers: plentiful waste fiber can be made valuable by electrospinning", *Cornell Chronicle*, http://www.news.cornell.edu/Chronicle/03/9.11.03/electrospinning_fiber.html, (Sep. 11, 2003),2 pages.

Langer, Robert, et al., "Designing materials for biology and medicine", *Nature*, vol. 428(6982), (Apr. 1, 2004),487-92.

Larsen, Gustavo, et al., "A Method for Making Inorganic and Hybrid (Organic/Inorganic) Fibers and Vesicles with Diameters in the Submicrometer and Micrometer Range via Sol-Gel Chemistry and Electrically Forced Liquid Jets", *Journal of the American Chemical Society*, 125(5), (Feb. 5, 2003), 1154-1155.

Lei, Huang, et al., "Generation of synthetic elastin mimetic small diameter fibers and fiber networks", *Macromolecules*, 33(8), (Nov. 1999),2989-2997.

Li, D, et al., "Direct Fabrication of Composite and Ceramic Hollow Nanofibers by Electrospinning", *Nano Letters*, 4(5), (May 2004),933-938.

Li, D, et al., "Electrospinning Nanofibers as Uniaxially Aligned Arrays and Layer-by-Layer Stacked Films", *Advanced Materials*, 16(4), (Feb. 26, 2004),361-366.

Li, D., et al., "Electrospinning of polymeric and ceramic nanofibers as uniaxially aligned arrays", *Nano Letters*, (3)8, (Jun. 20, 2003),1167-71.

Li, Dan, et al., "Fabrication of Titania Nanofibers by Electrospinning", *Nano Letters*, (3)4, (Feb. 20, 2003),1-6.

Liu, W, "Surface Coating of Poly(meta-phenylene isophthalamide) Nanofibers", *New Frontiers in Fiber Science, Spring Meeting*, (May 23-25, 2001).

Mironov, Artemi V., et al., "Nanofibers based on associating polyacrylonitrile-acrylamide copolymers produced by electrospinning", *2nd International Conference on Self-Assembled Fibrillar Networks (in Chemistry, Physics and Biology)*, Poster Session, Autrans, France,(Nov. 24-28, 2001).

Nanotechweb.org, "Nano fiber bandage could heal wounds", http://nanotechweb.org/articles/news/2/2/6/1, (Feb. 14, 2003),2 pages.

Physikalisch-Technische Bundesan, "Lotus Effect", *PTB Publication*, http://www.ptb.de/en/publikationen/blickpunkt/nanowelten/lotus.html, (Nov. 20, 2003),1 page.

Reneker, Darrell E., et al., "Bending instability of electrically charged liquid jets of polymer solutions in electrospinning", *Journal of Applied Physics*, 87, (May 1, 2000),4531-4547.

Weiss, P., "Thin jet flies two for one: double streams yield sheathed nanoballs, fibers", *Science News*, (Mar. 2, 2002).

Wuppertal Institute, "Dirt-repellant surfaces with lotus effect", http://www.wupperinst.org/FactorFour/best-practices/lotus-effect-short.html, (2003),1-3.

Zeiss, "The Lotus Effects of LotuTec", http://www.zeiss.de/4125680F0053A38D/ContentsWWWIntern/FE6774D035ABB49CC1256DF3003C7B36.

Grafe, Timothy, et al., "Polymeric Nanofibers and Nanofiber Webs: A New Class of Nonwovens", Presented at INTC 2002: International Nonwovens Technical Conference (Joint INDA-TAPPI Conference), Atlanta, GA, Sep. 24-26, 2002,13 pages.

"International Search Report for corresponding PCT Application No. PCT/US2005/026719", (File No. 20151),(Jan. 25, 2006),4 pgs.

"Final Office Action", U.S. Appl. No. 10/979,710, filed Nov. 2, 2004, (Aug. 28, 2006), 14 pgs.

"Non-Final Office Action", U.S. Appl. No. 10/979,710, filed Nov. 2, 2004, (Apr. 18, 2007), 20 pgs.

"Non-Final Office Action", U.S. Appl. No. 10/979,710, filed Nov. 2, 2004, (Mar. 7, 2006), 17 pgs.

Lewis, R. J., *Hawley's Condensed Chemical Dictionary*, (1997), pp. 246, 811-812.

* cited by examiner

COMPOSITE NANOFIBER MATERIALS AND METHODS FOR MAKING SAME

FIELD

The present invention relates to nanofiber materials, and, in particular, to composite nanofiber materials and methods for making same.

RELATED APPLICATION

This application is related to U.S. patent application Ser. No. 10/979,710, commonly assigned, filed on same date herewith and entitled, "Gradient Nanofiber Materials and Methods for Making Same," which is hereby incorporated herein by reference.

BACKGROUND

Products made from fibrous materials are useful in a wide variety of applications such as personal care products and garments, filtration devices, and the like. Such products can be absorbent or non-absorbent. These fibrous materials have specific surface chemistries and other material properties which affect their performance.

Absorbent products, for example, are used in a variety of applications from absorbent garments to wipe cloths. With absorbent products, it is important to have a sufficiently large surface area to allow for adequate absorption. In some instances, such as in absorbent garments, wicking is a very important feature. In many of these products it is desirable for the material to be either hydrophobic or hydrophilic, depending on its use. In some instances it is important for a product to have discrete areas with distinct properties.

Therefore, there is a need in the art to provide fibrous materials having improved properties.

SUMMARY

A composite material comprising a plurality of nanofibers intertwined with a plurality of coarse fibers to form one or more layers is provided. The nanofibers can be partially physically intertwined, i.e., entangled with one another in a multi-component material. Such intertwining can occur when both sizes of fibers are deposited substantially simultaneously in an overlapping region. The nanofibers can be any suitable type of nanofiber, including electrospun fibers, protein nanofibers, cellulose nanofibers, hollow nanofibers, bacterial nanofibers, inorganic nanofibers, hybrid nanofibers, splittable nanofibers and combinations thereof. The composite material can have a gradient in a thickness direction, a planar direction or both.

A composite material comprising a plurality of electrospun fibers intertwined with a plurality of coarse fibers to form a single layer is also provided. A composite material comprising a plurality of electrospun fibers combined with a plurality of coarse fibers to form a plurality of layers, i.e., a multi-layer material, is also provided. The single layer can have one or more planar gradients, while the plurality of layers can have one or more thickness gradients, one or more planar gradients or a combination thereof, i.e., gradients in the plane of the layers, and/or between one or more of the plurality of layers to form one or more thickness direction gradients, i.e., z-direction gradient (z-direction is the direction normal to the plane of the layers). In one embodiment, the plurality of electrospun fibers are produced from a single polymer or polymer blend and at least two types of electrospinning methods or from at least two different polymers or polymer blends and one or more types of electrospinning methods.

Any suitable materials can be used for the electrospun fibers. In one embodiment, polymers and/or polymer blends are used as the electrospun fibers, with no other materials present and/or only trace amounts of other fibers present, such as ceramics and/or titania. In one embodiment, the polymers and/or polymer blends are selected from the group consisting of polylactides, polylactic acids, polyolefins, polyacrylonitrile, polyurethane, polycarbonate, polycaprolactone, polyvinyl alcohol (PVA), cellulose, chitosan nylon (e.g., Nylon 6, Nylon 406, Nylon 6-6, etc.), polystyrene, proteins, and the like, or combinations thereof, further including combinations of polymers and polymer blends as described herein. Suitable solvents for each polymer, polymer combination or polymer blend can be selected from solvents known to those skilled in the art. In other embodiments, the electrospun fibers are made from materials other than polymers, such as ceramics.

Any suitable materials can be used for the coarse fibers. In one embodiment, the coarse fibers are selected from the group consisting of meltblown (MB) fibers, spun-bonded fibers, paper-making fibers, pulp fibers, fluff, cellulose fibers, nylon staple fibers, and any combinations thereof.

Embodiments of the invention further comprise a product having one or more components made from a composite electrospun material. The invention further comprises an absorbent article or other disposable article, health care product or consumer article made from a composite electrospun material having at least two types of electrospun fibers distributed non-uniformly to form one or more gradients. In one embodiment, at least one of the one or more gradients is a surface chemistry gradient, such as a contact angle gradient.

Embodiments of the invention further include a process comprising producing coarse fibers; producing nanofibers; and combining the coarse fibers and the nanofibers to produce a composite nanofiber material having one or more layers. In one embodiment, the nanofibers and coarse fibers are applied sequentially to the moving substrate. In one embodiment, the nanofibers and the coarse fibers are applied substantially simultaneously to the moving substrate, and, in one embodiment, are substantially intertwined in at least a portion of the resulting composite material. In one embodiment, the nanofibers and coarse fibers are joined in a coforming-like process in which the nanofibers are intermingled with the coarse fibers to form an intertwined composite web. In other embodiments one or more gradients are formed in the thickness and/or planar directions. In one embodiment, the nanofibers are electrospun fibers formed by any suitable method, including with the use of a needle and/or slot, or a plurality of needles and/or slots or orifices of any suitable shape and size.

Embodiments of the present invention are useful for any type of disposable garment, including, but not limited to absorbent articles such as diapers, training pants, adult incontinence, feminine care garments, and the like, as well as disposable articles such as hospital garments (defined herein to include surgical gowns, hair or head coverings (e.g., shower caps, hairnets, surgical caps, etc.), shoe covers, face masks, disposable patient gowns, laboratory coats, surgical gloves, and the like), other medical and surgical good including, but not limited to, sterile wrap, wound covers, hemostatic articles, further including any type of glove, glove liner, and so forth. Embodiments of the present invention are also useful for many other types of consumer products, including, but not limited to, wipes, air filters, water filters, absorbent pads, electrostatic webs, dust filters for computer media such as floppy disks and hard disks, and so forth.

Materials described herein can provide strong and varying surface effects, such as wicking. In one embodiment, hydrophobic fibers have a sufficiently small diameter to create a lotus effect.

DETAILED DESCRIPTION

Figure 1A:
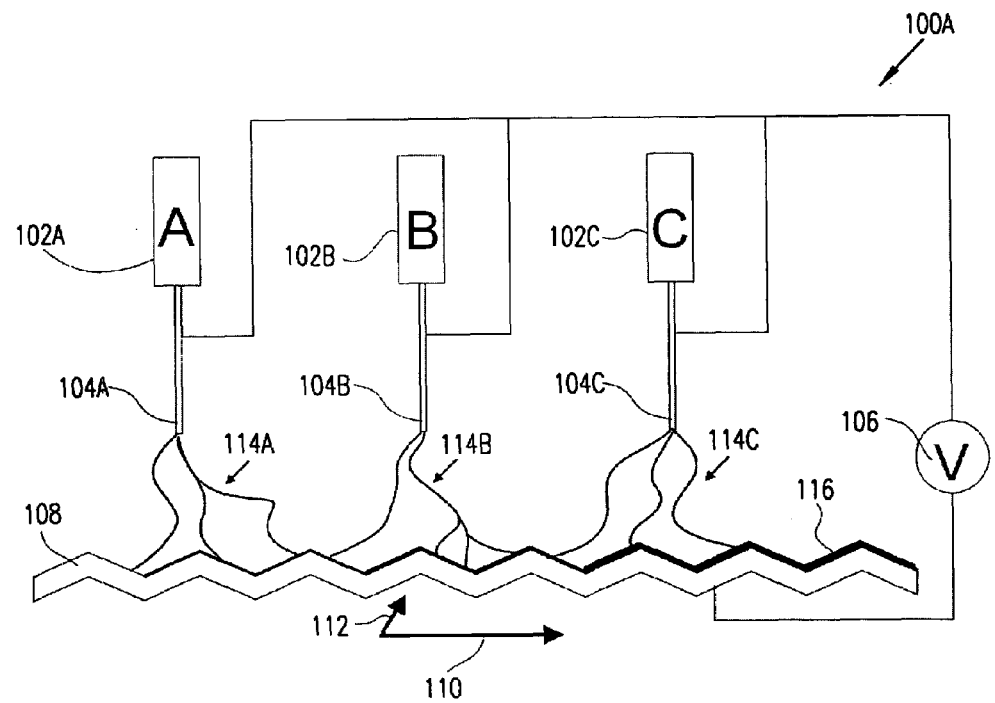
FIG. 1A is a schematic illustration of a process for forming a composite electrospun material in accordance with one embodiment of the present invention.

In the following detailed description of the preferred embodiments, reference is made to the accompanying drawings, which form a part hereof, and in which is shown by way of illustration specific preferred aspects in which the invention may be practiced. These embodiments are described in sufficient detail to enable those skilled in the art to practice the invention, and it is to be understood that other embodiments may be utilized and that electrical, chemical, mechanical, procedural and other changes may be made without departing from the spirit and scope of the present invention. The following detailed description is, therefore, not to be taken in a limiting sense, and the scope of the present invention is defined only by the appended claims, along with the full scope of equivalents to which such claims are entitled.

A composite material comprising a plurality of nanofibers, such as a plurality of electrospun fibers, and a plurality of coarse fibers is provided. In one embodiment, one or more gradients are present. A process for forming a composite material by combining nanofibers, such as electrospun fibers, with coarse fibers is also provided.

Definitions of certain terms used throughout the specification are provided first, followed by a description of various embodiments of the present invention, examples and a brief conclusion.

DEFINITIONS

As used herein, the term "disposable absorbent garment" refers to a garment that typically includes a bodyside liner and an absorbent element adapted for receiving and retaining body fluids or waste. The absorbent element typically includes an absorbent material such as cellulosic fibers, tissue layers, fibrous nonwoven webs and/or superabsorbent material. Often, such garments include a body chassis for supporting the absorbent element, which itself can include multiple components, such as an absorbent core, surge layer and so forth. Such garments include, for example, incontinence undergarments, which are typically configured with a self-supporting waist band, or diapers, and the like, which can be secured on the user with tabs, belts and the like. The body chassis can include a liquid permeable top sheet or film secured to an outer cover or backsheet, i.e., liner, which can be liquid permeable or impermeable, depending on whether an additional backsheet, i.e., barrier, is provided. Typically, the absorbent element is disposed between the body chassis and the user. The body chassis can take many forms, including for example, a pant-like or underwear type undergarment described herein, which includes a self-supporting waistband extending circumferentially around the waist of the user. Alternatively, the body chassis can be a diaper or like garment, which is secured around the user with various fastening means or devices known by those of skill in the are, including for example and without limitation tabs, belts and the like. The chassis can include elastic regions formed along the edges of the crotch region and around the leg openings, so as to form a gasket with the user's crotch and legs.

As used herein, the term "nonwoven web" refers to a structure or a web of material that has been formed without use of traditional fabric forming processes, such as weaving or knitting, to produce a structure of individual fibers or threads that are intermeshed, but not in an identifiable, repeating manner as is found in typical woven webs. Non-woven webs can be formed by a variety of conventional processes such as, for example, meltblowing processes, spunbonding processes, film aperturing processes, hydroentangling, coform production, airlaying, and staple fiber carding processes. Meltblown (MB) web and spunbond (SB) webs are both examples of "meltspun" webs.

As used herein, the term "coform" refers to a nonwoven material of air-formed matrix material comprising thermoplastic polymeric MB fibers and a multiplicity of individualized absorbent fibers, typically of at least microfiber size or larger, such as, for example, wood pulp fibers disposed throughout the matrix of MB fibers and engaging at least some of the MB fibers to space the MB fibers apart from each other. The absorbent fibers are interconnected by, and held captive within, the matrix of MB fibers by mechanical entanglement of the MB fibers with the absorbent fibers. The mechanical entanglement and interconnection of the MB fibers and absorbent fibers alone form a coherent integrated fibrous structure. The coherent integrated fibrous structure can be formed by the MB fibers and the absorbent fibers without any adhesive, molecular or hydrogen bonds between the two different types of fibers. The absorbent fibers can be distributed uniformly throughout the matrix of MB fibers to provide a homogeneous material. These materials can be prepared according to the descriptions in U.S. Pat. No. 4,100,324 to Anderson et al., U.S. Pat. No. 5,508,102 to Georger et al. and U.S. Pat. No. 5,385,775 to Wright, all commonly assigned, and hereby incorporated herein by reference.

As used herein the term "polymer" refers to and generally includes, but is not limited to, homopolymers, copolymers, such as, for example, block, graft, random and alternating copolymers, terpolymers, etc. and blends and modifications thereof. Polymers can include, but are not limited to, polylactides, polylactic acids, polyolefins, polyacrylonitrile, polyurethane, polycarbonate, polycaprolactone, polyvinyl alcohol (PVA), cellulose, chitosan nylon (e.g., nylon 6, nylon 406, nylon 6-6, etc.), polystyrene, proteins, and the like, or combinations thereof. Unless otherwise specifically limited, the term "polymer" is intended to include all possible geometrical configurations of the material. These configurations include, but are not limited to, isotactic, syndiotactic and random symmetries. Suitable solvents for each polymer can be selected from solvents known to those skilled in the art, including, but not limited to, sulfuric acid, formic acid, chloroform, tetrahydrofuran, dimethyl formamide, water, acetone, and combinations thereof. As used herein the term "polymer blends" refers to combinations of various types and amounts of polymers as well as blends of polymers with other materials, such as those described below.

Polymer blends or systems for forming fibers from single polymers can be selected from any suitable polymers, as can the corresponding solvents used in electrospinning. By way of example only, several representative polymer systems suitable for electrospinning include the following: Silk fibroin, optionally with added polymers such as poly(ethylene oxide) to improve processability or other properties, as disclosed by H. J. Jin et al., "Electrospinning Bombyx Mori Silk with Poly(ethylene oxide)," *Biomacromolecules,* Vol. 3, No. 6, November-December 2002, pp. 1233-1239; polyaniline in sulfuric acid or other solvents, optionally doped with a blend of polyaniline and polystyrene (PS) and/or polyethylene oxide (PEO) dissolved in a solvent such as chloroform, as disclosed by M. J. Díaz-de León, "Electrospinning Nanofibers of Polyaniline and Polyaniline/(Polystyrene and Polyethylene Oxide) Blends," *Proceeding of The National Conference on Undergraduate Research (NCUR)* 2001, University of Kentucky, Mar. 15-17, 2001, Lexington, Ky.; polyacrylonitrile-acrylamide (PAN-AA) copolymers dissolved in organic solvents, such as N,N-dimethylformamide (DMF), described by A. V. Mironov, "Nanofibers based on associating polyacrylonitrile-acrylamide copolymers produced by electrospinning," *2nd International Conference on Self-Assembled Fibrillar Networks (in Chemistry, Physics and Biology),* Poster Session, Autrans, France, Nov. 24-28, 2001. (Reported polymer concentrations ranged from 6.4 to 14.9 wt. % in DMF; Nylon 6 in formic acid, e.g., about 10-20% nylon in the solvent); polyurethane in a 1:1 mixture of tetrahydrofuran (THF) and dimethyl formamide (DMF), or other ratios of THF and DMF, ranging from 0 to 100% of either solvent. Polyurethane concentration may be, for example, from about 5% to 25% on a mass basis in the solvent; polyvinyl alcohol and/or PEO in water; and polylactic acid and biotin or other proteinaceous materials in a mixture of acetone and chloroform. Suitable solvents for each polymer blend or system can be selected from solvents known to those skilled in the art.

As used herein, the term "longitudinal," refers to or relates to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner," and "outer" as used herein are intended to indicate the direction relative to the user wearing an absorbent garment over the crotch region. For example, the terms "inner" and "upper" refer to a "bodyside," which means the side closest to the body of the user, while the terms "outer" and "lower" refer to a "garment side."

As used herein, the term "machine direction" or "MD" refers to the direction of travel of the forming surface or moving substrate onto which fibers are deposited during formation of a nonwoven fibrous material, such as the composite electrospun material of the present invention.

As used herein, the term "cross-machine direction" or "CD" refers to a direction which is essentially perpendicular to the machine direction defined above.

As used herein, the terms "meltblown fibers" or "MB fibers" or the letter "M" refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which can be to microfiber diameter. Thereafter, the MB fibers are carried by the high velocity gas stream and are deposited on a collecting surface to form a web of randomly disbursed MB fibers. Meltblown fibers are considered herein to be a type of "coarse" fiber.

As used herein, the term "spun-bonded fibers" or the letter "S" refers to fibers which are at least micro-sized fibers or larger and which are formed by extruding a molten thermoplastic material as filaments from a plurality of fine, usually circular, capillaries of a spinnerette with the diameter of the extruded filaments then being rapidly reduced as by, for example, by reductive drawing or other well-known spun-bonding mechanisms. The production of spun-bonded nonwoven webs is illustrated in patents such as, for example, in U.S. Pat. No. 4,340,563 to Appel et al., commonly assigned, and hereby incorporated herein by reference. Spun-bonded fibers are considered herein to be a type of "coarse" fiber.

As used herein, the term "coarse fibers" refers to fibers larger in size than nanofibers, to include microfibers as well as fibers larger than micro-sized fibers having diameters greater than about 100 microns, such as about 200 to about 500 microns or greater, with exemplary ranges of about 100 to about 2000 microns or about 200 to about 900 microns. Examples of coarse fibers include, but are not limited to, meltblown (MB) fibers, spun-bonded fibers, paper-making fibers, pulp fibers, fluff, cellulose fibers, nylon staple fibers, and the like.

As used herein, the term "microfibers" refers to small diameter fibers having an average diameter not greater than about 100 microns and not less than about 0.5 microns, with an exemplary range of about four (4) to about 50 microns. Examples of microfibers include, but are not limited to, meltblown (MB) fibers, spun-bonded fibers, paper-making fibers, pulp fibers, fluff, cellulose fibers, nylon staple fibers and the like, although such materials can also be made larger in size than microfiber-sized. Microfibers can further include ultra microfibers, i.e., synthetic fibers having a denier per filament (dpf) of between about 0.5 and about 1.5, provided that the fiber diameter is at least about 0.5 microns.

As used herein, the term "nano-sized fibers" or "nanofibers" or the letter "N" refers to very small diameter fibers having an average diameter not greater than about 1500 nanometers (nm). Nanofibers are generally understood to have a fiber diameter range of about 10 to about 1500 nm, more specifically from about 10 to about 1000 nm, more specifically still from about 20 to about 500 nm, and most specifically from about 20 to about 400 nm. Other exemplary ranges include from about 50 to about 500 nm, from about 100 to 500 nm, or about 40 to about 200 nm. In instances where particulates are present and heterogeneously distributed on nanofibers, the average diameter of a nanofiber can be measured using known techniques (e.g., image analysis tools coupled with electro microscopy), but excluding the portions of a fiber that are substantially enlarged by the presence of added particles relative to the particle free portions of the fiber.

As used herein, the term "electrospinning" refers to a technology which produces nano-sized fibers referred to as electrospun fibers from a solution using interactions between fluid dynamics and charged surfaces. In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymer solution or melt provided from one or more needles, slots or other orifices is charged to a high voltage relative to a collection grid. Electrical forces overcome surface tension and cause a fine jet of the polymer solution or melt to move towards the grounded or oppositely charged collection grid. The jet can splay into even finer fiber streams before reaching the target and is collected as an interconnected web of small fibers. Specifically, as the solvent is evaporating (in processes using a solvent), this liquid jet is stretched to many times it original length to produce continuous, ultrathin fibers of the polymer. The dried or solidified fibers can have diameters of about 40 nm, or from about 10 to about 100 nm, although 100 to 500 nm fibers are commonly observed. Various forms of electrospun nanofibers include branched nanofibers, tubes, ribbons and split nanofibers, nanofiber yarns, surface-coated nanofibers (e.g., with carbon, metals, etc.), nanofibers produced in a vacuum, and so forth. The production of electrospun fibers is illustrated in many publication and patents, including, for example, P. W. Gibson et al, "Electrospun Fiber Mats: Transport Properties," *AIChE Journal,* 45(1): 190-195 (January 1999), which is hereby incorporated herein by reference.

As used herein, the term "type" such as when referring to "different types of fibers" refers to fibers having "a substantially different overall material composition" with measurably different properties, outside of "average diameter" or other "size" differences. That is, two fibers can be of the same "type" as defined herein, yet have different "average diameters" or "average diameter ranges." (In the present invention, it is intended that fibers of different "average diameters" or "average diameter ranges," namely nano-sized fibers and coarse-sized fibers are used. Such fibers may or may not be of the same "type"). Although fibers are of different "types" when they have a substantially different overall material composition, they can still have one or more components in common. The "substantially different overall material composition" may be characterized in that at least one component comprising a first weight percent of at least 1 weight percent in a first fiber type (based on measurement of a representative sample size, such as a sample of at least 10 grams of collected fibers) has a substantially different second weight percent in a second fiber type, wherein the absolute value of the difference between the second weight percent and the first weight percent is at least the smaller of 5% and one-half of the first weight percent. Alternatively, the absolute value of the difference between the second weight percent and the first weight percent is at least the smaller of 10% and one-half of the first weight percent. The contact angle of the material in the first fiber type may differ from the contact angle of the material in the second fiber type by at least 10 degrees, more specifically by at least 20 degrees. For example, pure polyethylene oxide fibers and polyethylene oxide fibers coated with particles, such as silica colloidal particles or containing fillers, wherein the fillers are present at a level of 2 wt % or greater, may be considered two different "types" of fibers herein. Likewise, electrospun fibers made from a polymer blend with a first polymeric component present at a level of at least 10 wt % would be considered a different fiber type relative to electrospun fibers made from a polymer blend that was substantially free of the first polymeric component. Fibers of different "types" can also have a completely different content, each made of a different polymer for example, or one made from a polymer fiber and the other from a titania fiber, or a ceramic fiber and a titania fiber, and so on.

As used herein, the term "composite" or "composite nanofiber material" refers to a multi-component material containing fibers of at least two different "average diameters" or "average diameter ranges," namely coarse-sized fibers and nano-sized fibers. (Similarly, a "composite electrospun material" refers to a multi-component material containing fibers of at least two different "average diameters" or "average diameter ranges," namely coarse-sized fibers and electrospun fibers). The composite can be a non-gradient (uniform) composite having substantially equal distribution of fiber sizes and types throughout or it can be a gradient composite having varying amounts and/or placement of fiber sizes and types, as defined herein. The ratio of the average diameter size of the coarse fiber to the average diameter size of the nano-sized fiber can vary from about 5 times greater average diameter size to 10 times greater, to 20 times greater, to 50 times greater, to 100 times greater or more. The ratio of the surface area per unit mass of the nano-sized fibers to the surface area per unit mass of the coarse fibers can also be about 5 or greater, about 20 or greater, to about 100 or greater, such as from about 5 to about 1000, or from about 10 to about 200. The term, "composite" as used herein, therefore, is not intended to refer to a material having only fibers of different types with the same average diameter or average diameter range, i.e., either nano-sized fibers or coarse-sized fibers, but to a material having fibers with different average diameters or average diameter ranges, which may or may not be of the same type. As such, a material containing two "types" of nano-sized fibers, such as is described in U.S. patent application Ser. No. 10/979,710, commonly assigned, filed on same date herewith and entitled, "Gradient Nanofiber Materials and Methods for Making Same (hereinafter "Gradient Application"), is not considered herein to be a "composite" material, although some skilled in the art may refer to this as a type of "composite." Similarly, although some skilled in the art may also refer to two different "phases" in the same fiber as a composite (e.g., islands of a first polymer in a matrix of a second on a scale smaller than a fiber diameter or surface regions on a fiber relatively enhanced in concentration of one component relative to its concentration in the interior regions of the fibers), such fibers are not encompassed in the term "composite" as defined herein, but are otherwise considered to be two different "types" of fibers as defined herein.

As used herein, the term "gradient composite material" refers to a composite material containing one or more gradients (heterogeneity) in one or more directions, i.e., discrete areas having measurable differences resulting from the presence of fibers having different average diameters or average diameter ranges and/or from the presence of fibers of different types. For example, when fibers of at least two different average diameters or average diameter ranges and/or at least two different types are present, one or more may be present in varying amounts to create a gradient and/or one or more may or may not be present in varying amounts, but arranged to create a gradient. The gradient can be in the thickness or z-direction such that the material is a multi-layered material and/or in the planar or x/y-direction (CD or MD). The measurable differences found in a gradient can include, but are not limited to, differences in surface chemistry (e.g., wicking, contact angle, etc.) or other material properties, including, but not limited to density, pore size, surface charge, zeta potential, fiber diameter, and so forth. Materials having minor variations in fiber distribution, which do not cause differences in surface chemistry or other material properties, are not considered gradient composite materials. For example, for "gradient composite materials" containing electrospun fibers and coarse fibers, inherent non-uniform distribution of fibers due to the effects of the equipment used to create the electrospun fibers and/or the coarse fibers does not create a gradient as defined herein. Likewise, differences in density or basis weight of a given material from a single fiber type, possibly due to edge effects in producing the fibers (lower mass at the edges of the formation region) are not considered gradients. Likewise, differences within a single fiber due to multiple components in the fiber (e.g., bicomponent electrospun fibers, e.g., polymer/titania fiber) which may be called a "gradient" by persons skilled in the art, are generally not considered to alone produce a gradient composite material as defined herein, but may nevertheless be used as a single component thereof. Differences within a single electrospun fiber are produced, for example, by using two concentric needles to release a coaxial jet of two different fluids into an electrospinning environment. See, for example, "Hollow Nanofibers in a Single Step," *Chemical and Engineering News*, Vol. 82, No. 17, Apr. 26, 2004, p. 6 (non-hollow bicomponent fibers can be produced by similar means). A "composite electrospun material" which may or may not contain a gradient is to be distinguished from a "gradient electrospun material" (which contains a gradient but is not a composite material as defined herein) which is described in the Gradient Application, supra.

As used herein, the term "single layer of material" or "single-layered material" refers to a material composed of a single thickness which can be variable in size.

Figure 2A:
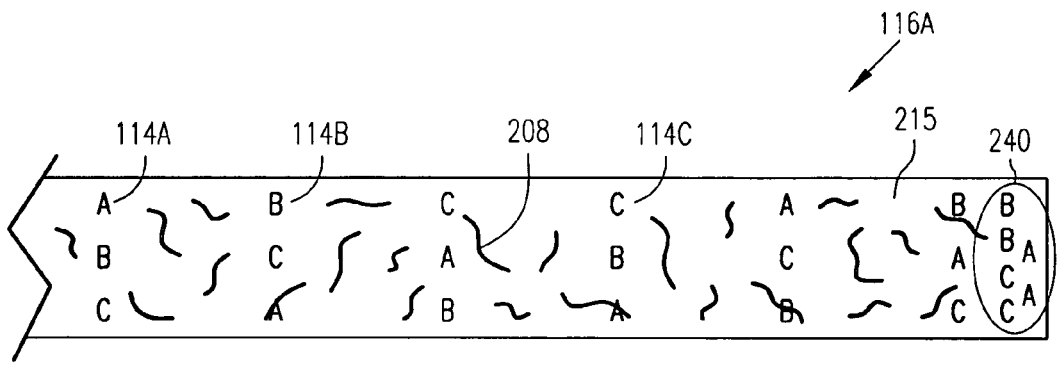
FIG. 2A is a simplified schematic illustration of a cross-section of a portion of a non-gradient composite electrospun material in accordance with one embodiment of the present invention.
Figure 2B:
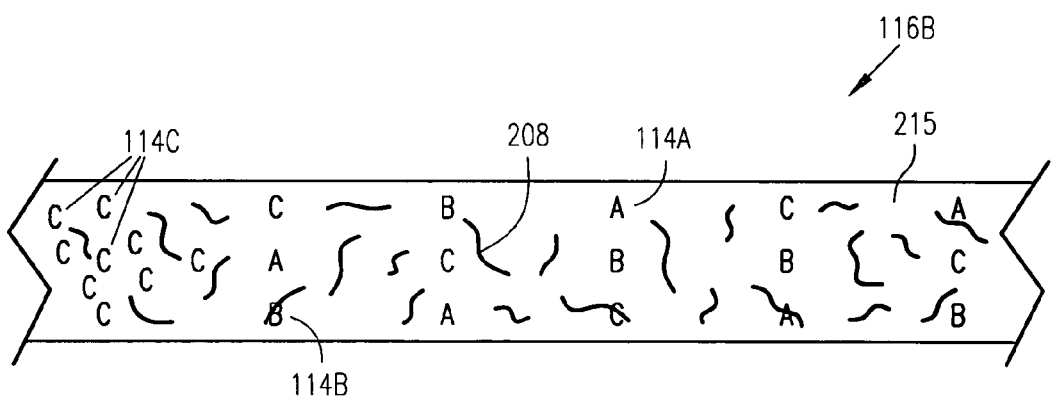
FIGS. 2B, 2C, 2D 2E and 2F are simplified schematic illustrations of cross-sections of portions of composite electrospun materials having one or more gradients ("gradient composite electrospun materials") in accordance with embodiments of the present invention.
Figure 2C:
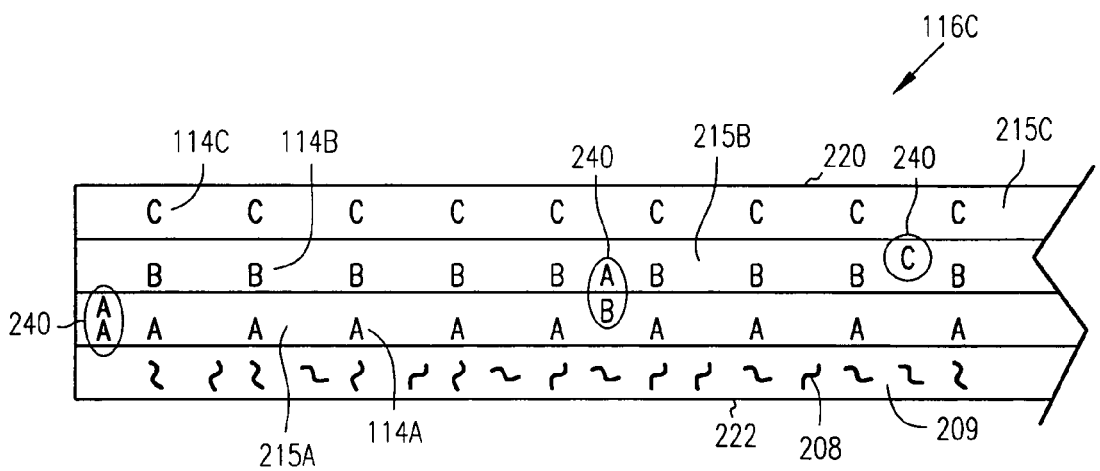

As used herein, the term "plurality of layers" or "multi-layered material" refers to a "stack" of single-layered materials, which in some instances, can have small areas of intertwining or blending between the layers (such as shown in FIG. 2C) that are not considered "gradients" as defined herein.

DESCRIPTION OF THE EMBODIMENTS

FIG. 1A provides a simplified schematic view of one embodiment of the present invention comprising a process for making a composite electrospun material 116. In the embodiment shown in FIG. 1A, the process utilizes a composite electrospinning system 100A which employs three polymer solutions, A, B, and C, provided in solution form from three different polymer sources or types, 102A, 102B, and 102C, respectively, which can be pressurized to be above atmospheric pressure. In this embodiment, each polymer source 102A, 102B and 102C is in fluid communication with a needle 104A, 104B, 104C, respectively, through which its respective polymer solution can be injected, although the invention is not so limited. In other embodiments some or all of the needles can be replaced with other dispensing means, such as slots (See FIG. 4). A voltage source 106 is joined to the needles 104A, 104B, 104C, such that the needles are at a substantially higher electrical potential than a collection substrate 108 as is understood by those skilled in the art. The voltage source applies a positive or negative charge to the needles. Alternatively, two or more voltage sources (not shown) can be used to independently control the voltage or two or more respective groups of needles or other orifices.

In another alternative embodiment, any or all of the needles 104A, 104B and 104C may be replaced with a slot or other orifice of any suitable shape or size. In another embodiment (not shown), the needles can comprise a metal body shielded with an outer insulating material (e.g., a dielectric coating), with the tip exposed to allow fluid to pass therethrough.

Although in this embodiment, three types of electrospun fibers 114A, 114B and 114C from three different polymer sources 102A, 102B and 102C, respectively, are being added in sequence onto a moving collection substrate 108, the invention is not so limited. Any number of different types of electrospun fibers can be combined with any number of coarse fiber types present, i.e., entrained, on the moving collection substrate 108 to produce a gradient or non-gradient composite material as described herein. In one embodiment one type of electrospun fiber is used in combination with one type of coarse fiber. In one embodiment, only one type of electrospun fiber is used with at least two types of coarse fibers. In another embodiment at least two types of electrospun fibers are used in combination with one or more types of coarse fibers. In yet other embodiments, more than three types of electrospun fibers are used with one or more types of coarse fibers.

The collection substrate 108 can be a fabric containing coarse fibers 208 (shown in FIG. 2), the surface of a roll or drum, an endless belt, and so forth, and can alternately comprise metal, such as a woven metal wire fabric or metallic coating, and can be electrically conductive (e.g., a woven or nonwoven web comprising electrically conductive polymers), although the invention is not so limited. Electrospinning can also be used to apply a low-basis weight functional coating applied uniformly or heterogeneously (e.g., in a pattern or with in-plane or z-directional gradients in chemistry) to one or both surfaces of a substrate such as a paper towel, a wound dressing, a disposable garment, a surgical gown, a glove, a shoe liner, a medical implant, an injection-molded device such as a catheter, filter materials (e.g., for air or water filtration) and so forth. In one embodiment, the collection substrate 108 is a three-dimensional textured fabric made from coarse fibers 208 (shown in FIGS. 2A-2E), such as a coform material. In the embodiment shown in FIG. 1A, the collection substrate 108 is moving in a machine direction (MD) 110, which is from left to right, while the cross-direction (CD) 112, which is normal to the MD, goes into the plane of the paper.

As the polymer solutions from polymer sources 102A, 102B and 102C are injected through the needles 104A, 104B and 104C at high electrical potential, nano-sized electrospun fibers 114A, 114B and 114C are formed by electrospinning as is understood by those skilled in the art. The electrospun fibers 114A, 114B and 114C are successively deposited onto the collection substrate 108 to form a composite electrospun material 116. Depending on the type and manner of this deposit, the resulting composite electrospun material 116 can be a non-gradient composite material, i.e., a substantially uniform single layered mat, or it can be a gradient composite material having heterogeneity in one or more directions, i.e., one or more gradients in one or more directions. Specifically, a gradient composite material made according to the process of FIG. 1A can have one or more gradients in the thickness direction (i.e., z-direction) and/or in the planar direction (i.e., x and/or y-directions), i.e., CD and/or MD.

In one embodiment the electrospun fibers 114A, 114B and 114C are entrained in an air flow provided by any suitable air flow source (not shown) during or after formation. The air flow carries the forming or formed electrospun fibers 114A, 114B and 114C into coarse fibers located on the moving substrate 108 that, in one embodiment, have not yet cooled. The solvent used to form the electrospun fibers 114A, 114B and 114C which is in solution with the respective polymers, can be, in one embodiment, partially vaporized by contact with the hot coarse fibers, such as any type of meltspun fibers. In one embodiment the solvent is recovered for use again in the system with any suitable type of vapor recovery system.

Figure 1B:
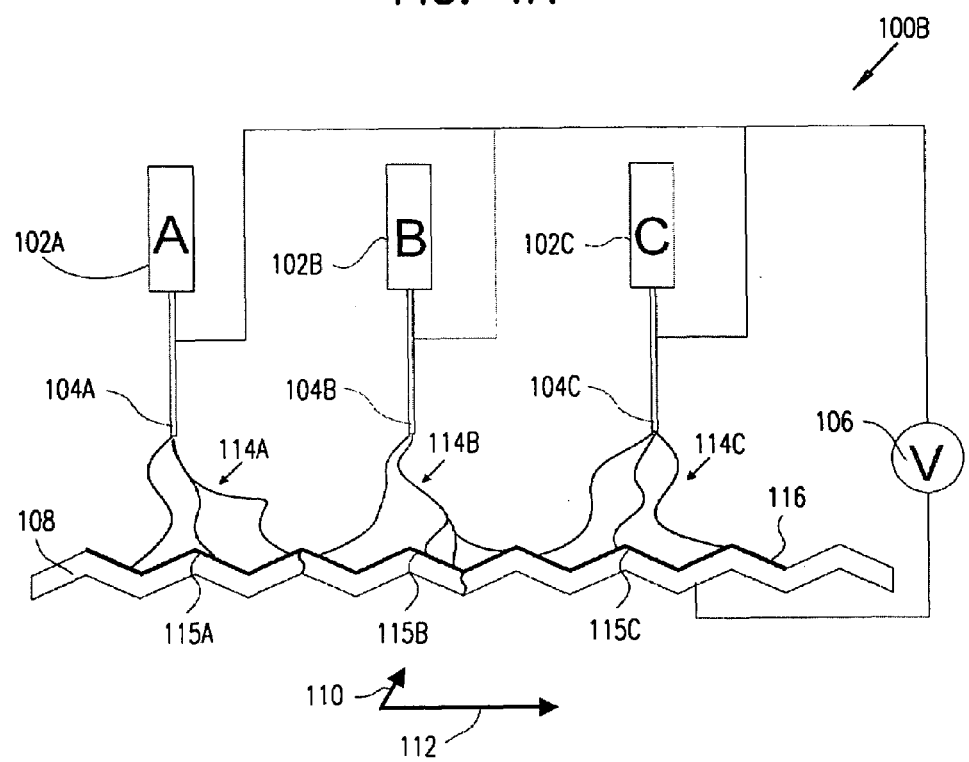
FIG. 1B is a schematic illustration of a process for forming a composite electrospun material in accordance with an alternative embodiment of the present invention.

FIG. 1B shows an alternative composite electrospinning system 100B in which the MD 110 goes into the plane of the paper and the CD 112 goes from left to right. Specifically, the collection substrate 108 is moving into the paper. Nano-sized electrospun fibers 114A, 114B and 114C are being deposited on the collection substrate 108 to form a composite electrospun material 116. In one embodiment, the fibers 114A, 114B and 114C are being deposited substantially simultaneously. Again, depending on the type and manner of the deposit, the resulting composite electrospun material 116 can be a non-gradient or a gradient composite material. In one embodiment, the composite electrospun material is a non-gradient composite electrospun material as shown in FIG. 2A with no distinct discrete areas. The presence of distinct discrete areas is dependent on many factors including the temperature of the polymers, the location and angle of the various polymers being deposited as nano-sized fibers, and so forth.

In the embodiment shown in FIG. 1B, the resulting composite electrospun material 116 is a gradient composite material having heterogeneity in at least the x or y-direction, i.e., a gradient which varies in the plane of the material 116, such that there are three laterally adjacent regions, i.e., discrete areas 115A, 115B and 115C, as shown, each having a relatively higher concentration of one of the three fiber types, 114A, 114B and 114C, respectively (See also FIG. 2B). In one embodiment, the electrospun gradient composite material also has heterogeneity in the z-direction (See FIG. 2C). In one embodiment, there are less than three discrete areas. In another embodiment there are more than three discrete areas.

Although the composite electrospun material 116 shown in FIG. 1B is a gradient composite material having identifiable discrete areas (115A, 115B and 115C), in practice, there can be at least some to significant overlap of the various fiber types in one or more regions which can blur the boundaries between discrete areas, although a gradient would still be present. (See, for example, FIG. 2E). The amount of overlap from one area to another is controlled in one embodiment by placement of the polymer sources 102A, 102B and 102C in relation to each other. Specifically, if the needle of one polymer type is angled towards another type, the resulting deposits from each can overlap. In other embodiments, one or more of the needles 104A, 104B and 104C or one or more of the polymer source and needle systems (102A/104A, 102B/104B, 102C/104C) are designed to move or oscillate in any suitable manner, such as back and forth, in a circular motion, up and down, and the like, either between various runs or during production to add additional heterogeneity to the electrospun material. The embodiment shown in FIG. 1B is also not limited to the number or placement of polymer types shown and in other embodiments, various combinations of electrospun fiber types and coarse fiber types (including non-polymeric types) can be used to produce either a non-gradient or gradient composite electrospun material as desired.

As discussed above, in one embodiment, the composite electrospun material 116 produced according to the process of either FIG. 1A or FIG. 1B or any combination thereof, is a non-gradient composite electrospun material such as the material 116A shown in FIG. 2A having a single layer 215. In this embodiment, the process is essentially a coforming-like process in which coarse fibers are intermingled with nanofibers (rather than other types of coarse fibers) to form an intertwined composite web. Such embodiments, in which the various fiber types are combined together to form a unique blend of composite fibers, i.e., a non-gradient composite electrospun material, do not require any type of bonding or laminating, and therefore do not require special consideration which may otherwise be important, when using materials having varying properties.

FIG. 2A is intended to provide a simple illustration of general trends within the material 116A. The non-gradient composite electrospun material 116A with no heterogeneity in either direction can be formed from any number of fiber sizes and types. Conditions must be adjusted, however, to allow for the substantially even distribution of all fibers within a single layer or mat such that the bulk property is substantially the same throughout the material (as opposed to discrete distribution of the bulk property in certain zones or areas as in a gradient material). As FIG. 2A shows, in this embodiment, the various fibers (114A, 114B, 114C and 208) are distributed substantially uniformly throughout a single layer, although minor variations can be present throughout the layer which do not affect surface properties, such that the material is not considered to have a gradient.

FIGS. 2B, 2C, 2D and 2E illustrate exemplary gradient composite materials which can be produced according to the processes of either FIG. 1A or FIG. 1B or combinations and/or modifications thereof, including any suitable process adapted to produce a gradient composite material. As with FIG. 2A, FIGS. 2B, 2C 2D and 2E are also intended to provide simple illustrations of general trends within the materials 116B, 116C, 116D and 116E, respectively. Such materials can have gradients in the z-direction and/or in the x and/or y-direction, i.e., in the plane of the material, e.g., with measurable gradients in the machine direction, cross-direction or other in-plane direction. For example, these gradients or zones can contain fibers that are independently hydrophobic, hydrophilic, elastomeric, non-elastomeric, highly porous, less porous, and so forth. The basis weight, fiber diameter, and so forth can also vary with position. For example, one side of an electrospun material can be an electrospun web combined with hydrophilic cellulose coarse fibers, while another side or region is combined with a sufficient amount of a different type of fiber or fibers such as coarse nylon staple fibers or other cellulosic fibers, such that the resulting composite electrospun material differs in at least one direction in surface chemistry or other material property, thus yielding a gradient material.

In one embodiment, a material property of the composite electrospun material 116 averaged over an approximately 1-centimeter (cm) by 1-cm area square area in the material varies in the plane of the material such that the average parameter varies substantially monotonically along a linear path of about 5 cm in length (alternatively, of about 3 cm in length or about 10 cm in length) such that the average property at the beginning of the path differs by more than a predetermined value (e.g., by about 20% or about 50% of the higher of the two values) from that at the end of the path. For example, a contact angle gradient includes a gradient having measurable differences in the contact angle, wherein the average contact angle averaged over an approximately 1 cm square region in the composite electrospun material 116, such as a composite electrospun web, is about 20 degrees in one portion of the web, and then rises along a linear path in the web reaching a portion of the web that is relatively more hydrophobic, such that a region about 5 cm away from the first region may have an average contact angle of about 60 degrees, or, more generally, may differ by about 20 degrees or more. In other embodiments, the average fiber size varies by about 30% or more, or by about 100% or more, along an approximately 5-cm path in the plane of the composite electrospun material 116. For z-direction gradients, fiber properties averaged over a stratum of the composite electrospun material 116 representing about 20% of the thickness of the material varies from adjacent strata by about 20% or more or about 50% or more of a physical property such as fiber diameter or surface energy, or by about 20 degrees or more for contact angle.

The gradients can be formed in any suitable manner, such as by varying the source location and/or rate and/or angle of delivery of one or more types of fibers being added to the moving substrate, including oscillating the electrospun delivery means such as the needle, varying the rate of production and/or distribution of fibers, varying the speed of the moving collection substrate, varying polymer temperatures, varying the applied voltage, varying the electrospun fiber characteristics (e.g., needle characteristics, use of slots, etc.), and so forth. Any of these parameters can be varied in time as well, to create MD variations. In one embodiment, the gradient composite materials of the present invention have a surface chemistry gradient, wherein the high surface area of electrospun fibers coupled with the measurable differences in surface chemistry across the material, provides a material with regions of super-hydrophilicity and/or super-hydrophobicity, including optional regions that repel liquids according to the "lotus effect" discussed herein.

For example, if the process of either FIG. 1A or FIG. 1B is performed in a manner to create a single layered material as described in FIG. 2A, but at least one component, such as electrospun fiber 114C, is deposited in such a manner to cause it to have a higher concentration in a particular area, this can create a gradient, i.e., heterogeneity, in the x or y-direction, i.e., in the plane of the material, such as is shown in FIG. 2B. Such a material is still considered to have a single layer 215, but can also have a gradient within that layer. Any number of gradients can be present in the plane of the single-layered material.

Figure 2D:
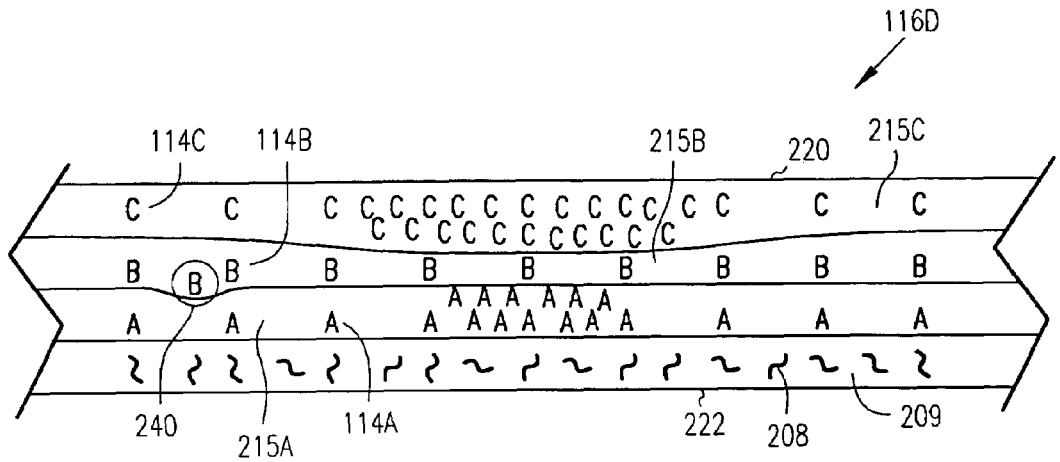

However, not all non-uniform areas are considered "gradients" as defined herein. For example, non-uniform areas 240 near the edge of the single-layered material in FIGS. 2A and 2C and near the top or bottom of a layer in FIGS. 2B, 2C and 2D are not considered to be gradients as defined herein. Non-uniform areas 240 can occur inherently during the process of making any type of composite material as is known in the art. In some instances, the non-uniform areas 240 shown in FIG. 2A (and the non-uniform area (AA) 240 shown near one edge in FIG. 2C) may be caused by several factors, including what is known as an "edge effect" wherein the concentration or basis weight of one material tapers away at the edge of a region in which the material is applied. Other non-uniform areas 240 are areas of limited intertwining between layers, such as the "C" and "A/B" non-uniform areas 240 shown in FIG. 2C. Yet other non-uniform areas 240 produce some variation in thickness of a layer, such as the "B" non-uniform area of FIG. 2D.

In contrast to FIG. 2B, FIG. 2C shows a material 116C which can be made according to the process of FIG. 1A when performed in a manner to cause a multi-layer material to form, i.e., a gradient in the z-direction. In this material 116C, there is a bottom layer 209 made of coarse fibers 208 and a top layer 215C made of electrospun fibers 114C. The bottom layer 209 has a bottom surface 222 and the top layer 215C has a top surface 220. In between these two layers are two additional layers, 215A and 215B, comprised of electrospun fibers, 114A and 114B, respectively. Any variation of this layering is possible, such that in some embodiments, for example, the top layer is comprised of two or more types of electrospun fibers and the bottom layer is comprised of a combination of electrospun and coarse fibers. Any number of other combinations as well as any number of layers and layering patterns are possible, depending on the desired properties of the material. In one embodiment, the material 116C of FIG. 2C is made according to the process of FIG. 1B by providing means for depositing the various electrospun fibers (114A, 114B and 114C) in a sweeping manner to cause coverage throughout the length and width of the material, and by adjusting the timing of the deposits of the fibers 114A, 114B and 114C to allow for successive deposition of the fibers rather than depositing the fibers substantially simultaneously.

FIG. 2D shows a multi-layered material 116D having gradients in the z-direction as well as gradients in at least two planes, namely layers 215A and 215C, as shown. Material 116D is most likely made according to the process of FIG. 1A, although the invention is not so limited and such a material can also be made according to the process of FIG. 1B with suitable adjustments, as described above. The thickness and basis weight of individual layers may also vary with position as shown with layer 215C while in other embodiments, the higher concentration of a particular component, such as 114A in layer 215A does not necessarily cause any substantial change in the thickness of the layer. In this material 116D, there is a bottom layer 209 made of coarse fibers 208 and a top layer 215C made of electrospun fibers 114C. The bottom layer 209 has a bottom surface 222 and the top layer 215C has a top surface 220. In between these two layers are two additional layers 215A and 215B comprised of electrospun fibers 114A and 114B, respectively. Any variation of the layer numbers and/or layering pattern is possible, as described above.

Figure 2E:
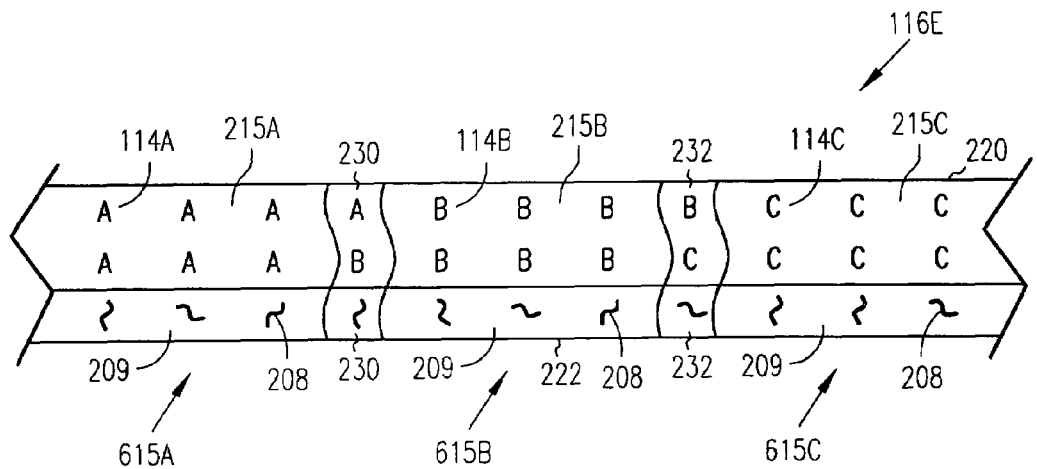

FIG. 2E shows a material 116E also having gradients in both the thickness and planar directions. Material 116E can be produced by the process of FIG. 1B, although the invention is not so limited. Suitable modifications could likely also be made to the process of FIG. 1A to produce material 116E. In the material 116E shown in FIG. 2E, there is a multi-sectioned bottom layer 209 made of coarse fibers 208 and a multi-sectioned top layer 215A, 215B and 215C each containing its respective electrospun fibers 114A, 114B and 114C. The bottom layer 209 has a bottom surface 222 and the top layer 215C has a top surface 220. In this embodiment, there are also two areas of overlap that extend throughout the top and bottom layers, namely Area A/B 230 and Area B/C 232, each of which contains more than one type of electrospun fiber as shown. Such areas of overlap can be made as small or as large as desired, depending on the final properties desired but are not considered to be a gradient as defined herein. Any variation of the layer numbers and/or layering pattern is also possible, as described above.

Figure 2F:
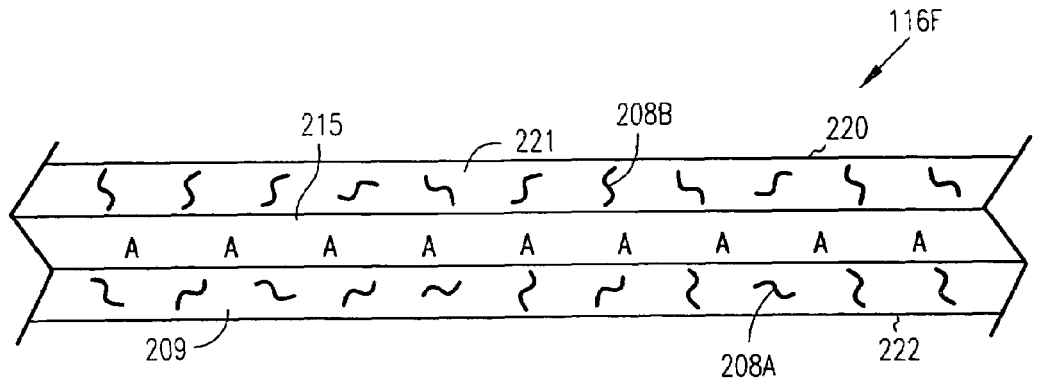

The processes of the present invention can also be used to make composite "analogs" of known materials, e.g., "spunbonded/meltblown/spun-bonded" (SMS) material. A "composite analog" refers to a composite material having at least one known component substituted with a nanofiber, such as an electrospun fiber, and includes "coform analogs" made using "coform-like" processes as described herein. For example, a subsequent layer of coarse fibers can be added onto the top of one or more layers of electrospun fibers by any means known in the art, such that the one or more layers of electrospun fibers are essentially sandwiched in between two layers of coarse fibers as shown in FIG. 2F. In this particular embodiment, material 116F has a bottom layer 209 made of one type of coarse fibers 208A and a top layer 221 made of another type of coarse fibers 208B. The bottom layer 209 has a bottom surface 222 and the top layer 221 has a top surface 220. In between these two layers is a middle layer 215 comprised of electrospun fibers 114 of type "A". Any variation of the layer numbers and/or layering pattern is possible, as described above. In one embodiment, both the bottom and top layers are the same, e.g., spunbond (S) layers, with the middle layer being any type of nanofiber (N) rather than a traditional meltblown (M) layer.

In another embodiment, the composite analog is produced by adding two or more types of coarse fibers onto the moving substrate prior to the addition of the electrospun fibers. Such an analog can, in one embodiment, take the form of SMN, with the nanofiber layer (N) replacing a traditional spunbond layer, and the middle meltblown layer (M) serving as a bridging layer between the spunbond layer (S) and the nanofiber layer (N). Such composites can also take the form of SNS, SMNMS, NMN, NM, SN, and the like. Film or tissue layers or other webs (e.g., coform) can also be present. As with the embodiments described above, the electrospun fibers present in a composite analog can be distributed either uniformly or non-uniformly in the plane of the material and can also be combined with fibers from wood or other particulates.

Although relatively simple gradients in primarily the thickness direction and/or the planar direction have been discussed and illustrated, in practice, more complex gradients of other kinds can be formed in any other number of configurations as well according to manufacturing practices known in the art, including suitable modifications of any of the processes discussed herein and shown in FIGS. 1A, 1B, 3 and 4. For example, in one embodiment a radial gradient composite electrospun material is used with a central region of one chemistry type fading radially outwardly, where it is replaced by a second region of a second chemistry type; a thickness direction gradient can also be simultaneously present in some regions. Gradients can occur in a repeating or non-repeating pattern within the material, such as a staggered grid array of one surface type surrounded by another. In one embodiment a rectilinear or hexagonal pattern is used. In other embodiments a pattern of stripes, dots or other known configurations is used. In yet other embodiments the gradients are linear, oval, or can correspond to a digital image achieved by printing of surface treatments. Any number and type of gradients can be combined into one material as desired and/or into one product using different types of materials.

Generally speaking, homogenous composite materials containing no gradient in either direction such that the nanofibers are distributed substantially uniformly in a single plane of the material, as illustrated in FIG. 2A, may be useful for layers in absorbent cores, bodyside liners, wound dressings, face masks, disposable garments and the like.

Gradient composite materials having a gradient in just the x and/or y-directions, i.e., a single layered material with one or more planar gradients, as illustrated in FIG. 2B, may be useful in products such as absorbent articles or medical articles which control wicking of fluid from one region to another, or that serve to provide barrier properties (e.g., against fluids such as alcohol, blood, or other bodily fluids, or against microbes and viruses in particular) in some regions of an article while allowing fluid passage or intake in other regions.

Gradient composite materials having a gradient in just the thickness or z-direction, as illustrated in FIGS. 2C and 2F may be useful for fluid intake layers, barrier layers, skin-contacting materials, and filters for air, water or other fluids.

Gradient composite materials having one or more gradients in both the z-direction and within the plane, as illustrated in FIGS. 2D and 2E may be useful for a variety of medical articles and disposable garments.

Figure 3:
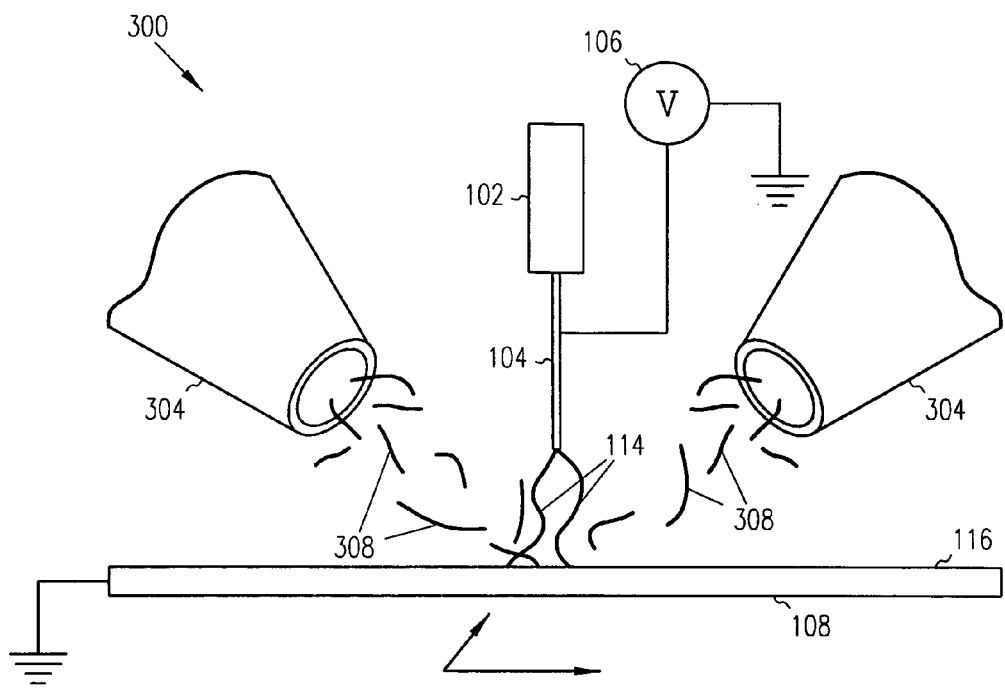
FIG. 3 is a schematic illustration of an alternative process for forming a composite electrospun material in accordance with one embodiment of the present invention.

FIG. 3 provides a simplified schematic view of an alternative process for forming a composite electrospun material 116 in which coarse fibers are deposited onto an electrical grid during fiber formation as electrospun fibers are also being deposited. The process utilizes a composite electrospinning system 300 in which electrospun fibers 114 from a single source of polymer solution 102 (which can be pressurized to be above atmospheric pressure) are combined with coarse fibers 308 exiting two separate coarse fiber delivery devices 304. In one embodiment, the electrospun fibers 114 are entrained by air and combined with the coarse fibers 308 also entrained by air, i.e., discrete cooled fibers, as they are being formed. The intertwined fibers are then deposited on the moving substrate 108, thus forming a non-gradient composite electrospun material. In another embodiment, the formation of at least some of one of the fiber types is timed such that one is formed first and deposited on the moving substrate 108. In this embodiment, the two fiber types (electrospun fibers 114 and coarse fibers 308) combine on the moving substrate 108, which can, in some embodiments, result in a gradient composite material 116. In one embodiment, at least some of the coarse fibers 308 are formed sufficiently prior to the formation of the electrospun fibers 114 such that they are cooling from a molten state when combined with the electrospun fibers 114.

In practice, any suitable number of polymer solutions 102 and any number of coarse fiber delivery devices 304 can be used. In the embodiment shown in FIG. 3, the single source of polymer solution 102 is in fluid communication with a single needle 104 for delivering a stream of the solution. The voltage source 106 is used to place the needle 104 at a different electrical potential than the collection substrate 108 as is understood by those skilled in the art. In the embodiment shown in FIG. 3, the collection substrate 108 is grounded, although the invention is not so limited. The collection substrate 108 can be moving in or out of the plane of the paper, and can be substantially porous such that air can readily pass through it while it collects the air-entrained fibers. The fiber delivery devices 304 are capable of delivering coarse fibers 308 entrained in a jet of air moving at any suitable speed, such as about 1 to 100 m/sec. In one embodiment the fiber delivery devices 304 are nozzles.

In one embodiment, the voltage potential of the target surface, i.e., the moving substrate 108, oscillates rapidly, such that electrospun fibers 114 which are initially pulled toward the grounded surface can be repelled milliseconds later to allow gas flow of air or other suitable gases, to help carry the electrospun fibers 114 into a stream of coarse fibers 308 as they are being formed. In another embodiment, the electrospun fibers 114 are not directed away from the grounded target surface, i.e., the moving substrate 108, but are combined with the coarse fibers 308 from the adjacent fiber delivery devices 304 to form an intermeshed complex.

Such combinations of electrospun and coarse fibers can be used to produce non-gradient materials (i.e., intertwined composites) or materials having gradients in the plane of the resulting material (CD or MD) or in the thickness direction of the material, or both, depending on the placement of the electrospinning needles 104 and the fiber delivery devices 304 as well as the extent of electrostatic and pneumatic forces being used. In one embodiment, the fibers 308 delivered by the fiber delivery devices 304 comprise two or more fiber types, and can also have substantially different surface chemistry and other properties than the electrospun fibers 114. Any of the materials described in FIGS. 2A-2F can also be produced according to the methods of FIG. 3, as well as any variations thereof.

The collection substrate 108 in any of the processes described herein can be moving at any useful speed in the MD, such as about 0.1 to about one (1) cm/sec or greater. In one embodiment, the MD speed is greater than about one (1) cm/sec up to about 400 cm/sec or greater. Generally, the slower speeds are useful for producing gradient composite materials with machine direction gradients controlled by dynamically modifying fiber-producing conditions during production, while the higher speeds are useful for steady-state products or materials with gradients in the cross-machine direction (CD) achieved by generating fibers (coarse or electrospun) from two or more sources spaced apart in the cross-direction, or for producing z-direction gradients under steady-state conditions, although any suitable speed can be used as desired. Similar principles apply in the manufacture of non-gradient composite materials. In one embodiment, the speed ranges from about five (5) to 200 cm/sec. In another embodiment, the speed ranges from about 0.1 to about 50 cm/sec. In another embodiment, the speed ranges from about 0.5 to ten (10) cm/sec. In one embodiment, the speed is varied during the operation, i.e., in time, to allow for varying amounts of fibers to be deposited in the MD.

The electrospun fibers themselves can be produced by varying methods as is known in the art, to alter specific measurable properties as desired, thus creating different "types" of fibers as defined herein. In one embodiment a complex electrode system is used to produce the electrospun fibers comprising slots or openings (instead of or in addition to needles) for high shear gas flow to entrain the electrospun fibers. Useful geometries can then be adapted such as uniaxially aligned ceramic electrospun fibers as described by Li, et al, in "Electrospinning of Polymeric and Ceramic Nanofibers as Uniaxially Aligned Arrays," *Nano Letters*, vol. 3, no. 8, Jul. 8, 2003, pp. 1167-1171, hereby incorporated herein by reference. In other embodiments titania nanofibers or alumina-borate oxide fibers are produced, which can also be aligned, if desired. Additionally, ceramic nanofibers comprising titania/polymer or anatase nanotubes can also be used, such as those described by Dan Li, et al., in "Direct Fabrication of Composite and Ceramic Hollow Nanofibers by Electrospinning," *Nano Letters*, vol. 4, no. 5, Mar. 30, 2004, pp. 933-938, hereby incorporated herein by reference.

Figure 4:
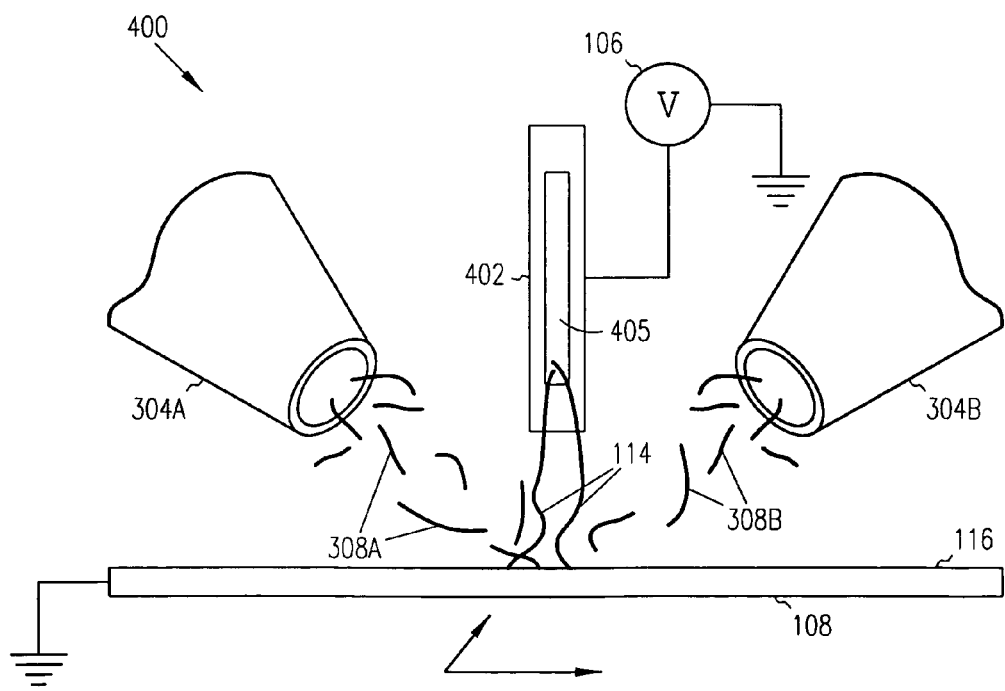
FIG. 4 is a schematic illustration of another alternative process for forming a composite electrospun material in accordance with one embodiment of the present invention.

In the embodiment shown in FIG. 4, for example, the needle 114 of FIG. 3 is replaced by a slot 405. In some embodiments, the resulting electrospun fibers 114 have different properties than electrospun fibers produced with the same polymer through a needle. Additionally, in this embodiment, two different coarse delivery devices, 304A and 304B, are producing two different types of coarse fibers 308A and 308B. Otherwise the system 400 of FIG. 4 is generally the same as FIG. 3 above and operates to produce a composite electrospun material 116. Such a system can also be used in conjunction with the systems of FIGS. 1A and 1B. Again, any of the materials shown in FIGS. 2A, 2B, 2C, 2D, 2E and 2F, as well as any variations thereof, can also be produced by the method of FIG. 4.

In another embodiment, the grounding electrode is a rotating, translating or stationary grounded surface with slots to allow aerodynamic forces to overcome the electrostatic attraction to the grounded surface, thereby allowing electrospun fibers to be blended into a stream of coarse fibers. In yet another embodiment, the electrospinning process is performed in a vacuum. Other methods can produced branched fibers, tube fibers, nanoballs, ribbon fibers, split fibers, electrospun yarns, and surface coated fibers, as is known in the art.

In one embodiment, filler materials and other solids such as any type of particle (e.g., superabsorbent particles, odor control materials such as talc, zeolites or activated carbon particles or silica, opacifiers, graphite, graphite nanoparticles, carbon nanotubes, silica nanoparticles, colloidal metals such as silver or gold, etc.), as well as kaolin or other minerals or fillers, antimicrobials, elastomeric materials such as elastomeric polyurethanes and the like, are embedded in the composite electrospun material to create fibers of different types (when the filler materials are present at a level of 2 wt % or greater of the total weight of the fiber plus filler material combined) as compared with fibers of the similar material composition but without filler materials. Such materials can be useful in providing skin-health benefits in skin-contacting layers of garments or in absorbent articles, or for providing a variety of other benefits in consumer goods.

Methods of attaching superabsorbent particles or other particles to fibers using binders are disclosed in U.S. Pat. No. 6,596,103, "Method of Binding Binder Treated Particles to Fibers," issued Jul. 22, 2003 to Hansen et al. and U.S. Pat. No. 6,425,979, "Method for Making Superabsorbent Containing Diapers," issued Jul. 30, 2002 to Hansen et al., both of which are hereby incorporated herein by reference. Mechanical means for delivering superabsorbent particles to a structure via air entrainment are disclosed in U.S. Pat. No. 6,709,613, "Particulate Addition Method and Apparatus," issued Mar. 23, 2004 to Chambers et al., hereby incorporated herein by reference.

Superabsorbents useful in embodiments of the present invention can be chosen from classes based on chemical structure as well as physical form. These include, for example, superabsorbents with low gel strength, high gel strength, surface cross-linked superabsorbents, uniformly cross-linked superabsorbents, or superabsorbents with varied cross-link density throughout the structure. Superabsorbents may be based on chemistries that include, but are not limited to, poly(acrylic acid), poly(iso-butylene-co-maleic anhydride), poly(ethylene oxide), carboxymethyl cellulose, poly (vinyl pyrrollidone), poly(-vinyl alcohol), and the like. Other details regarding the use of superabsorbent particles for absorbent articles are disclosed in U.S. Pat. No. 6,046,377, "Absorbent Structure Comprising Superabsorbent, Staple Fiber, and Binder Fiber," issued Apr. 4, 2000 to Huntoon et al., and U.S. Pat. No. 6,376,011, "Process for Preparing Superabsorbent-Containing Composites," issued Apr. 23, 2002 to Reeves et al., both of which are hereby incorporated herein by reference.

In one embodiment elastomeric fibers, such as elastomeric polyurethanes, are used to create breathable stretchable films. In one embodiment a layer of electrospun nanofibers are deposited on a film or nonwoven web, such as an apertured film or elasticized web, in order to provide a breathable moisture barrier layer attached to a layer providing other functionality, such as texture, elasticity, integrity or bulk. In an alternative embodiment, the electrospun fibers are deposited on a rubbery elastomeric web to improve the tactile properties of the material. Elastomeric-containing materials are useful in products such as diapers, training pants, feminine napkins, hospital gowns, wraps for placement on the body, sterile wrap, wound dressings, articles of clothing, wipes for surface cleaning, athletic gear, and the like.

In one embodiment, a small amount of conductive polymer is added to the electrospun fiber to provide ions in the gas or melt phases. The conductive polymer can also serve as an initial layer on the collecting substrate to help modify or control the electrical field or modify the formation of the electrospun material. In a particular embodiment, about one (1) to about five (5) %, by weight, conductive polymer material is added to the electrospun fiber. In one embodiment, the conductive polymer is a 5-membered ring which includes a nitrogen, such as polypyrliodne, and the like. The use of conductive polymers is useful in biosensor applications, such as wetness sensors and the like.

In one embodiment, some or all of the composite electrospun material comprises hydrophobic fibers of sufficiently small diameter to simulate the lotus effect in their hydrophobicity and self-cleaning abilities. The lotus effect refers to the lotus leafs extreme hydrophobicity, wherein minute hydrophobic bumps on the surface allow water and other liquid to roll off the surface. Known commercial mimicry of the lotus effect has relied on nanoparticles, such as small particles of wax, arranged as small bumps on a surface. In embodiments of the present invention, nanofibers are used as the hydrophobic fibers. See, for example, U.S. Pat. No. 6,660,363 to Barthlott and U.S. Patent Application 2002/0150724 to Nun et al., both of which are hereby incorporated herein by reference.

The resulting composite electrospun materials are most often webs. Such webs can be textured (e.g., molded to a three-dimensional shape, such as by forming against or subsequently molding against an Uncreped Through-Air Dried (UCTAD) fabric, such as the "ironman" design known in the art), apertured, slit, embossed, colored, combined with other materials, such as other absorbent materials in layered structures, joined to elastomeric webs and so forth. Additionally or alternatively, some or all portions of the materials can be chemically treated after at least some of the electrospun fibers have been deposited to modify surface chemistry and to optionally create or enhance surface chemistry gradients in the web. Such treatments can include, for example, fluorochemicals.

In one embodiment, the material is a composite web comprising from about one (1) to about 99% electrospun fibers, by weight, from zero (0) to about 99% papermaking fibers, by weight, and from zero (0) to 99% meltspun fibers, such as polyolefins, coarse bicomponent fibers, and the like, by weight.

In addition to electrospun fibers, it is also possible to use other types of nanofibers in any of the various embodiments described herein. For example, in one embodiment hollow nanofibers are used for improved thermal insulation, acoustic insulation, dialysis materials, membrane filtration, reverse osmosis filters, chemical separations, etc. Formation of hollow nanofibers can be achieved by a technique described by I. G. Loscertales et al, in *J. Am. Chem. Soc.* 126, 5376 (2004), hereby incorporated herein by reference, which yields hollow fibers with nanometer-sized interior diameters in a single step. The method exploits electrohydrodynamic forces that form coaxial jets of liquids with microscopic dimensions. By the injection of two immiscible or poorly miscible liquids through a pair of concentric needles at high voltage, coaxial jets of liquids are formed. An outer shell solidifies around an interior liquid that can be evaporated or otherwise removed after the fibers are formed, yielding hollow fibers. With this method, hollow silica fibers can be spun with fairly uniform-sized inner diameters measuring a few hundred nanometers. The shells can be formed via sol-gel chemistry from tetra-ethylorthosilicate around cores of common liquids such as olive oil and glycerin. Many other compounds, such as ceramic materials and ceramic polymer combinations, can also be used to form hollow fibers.

In another embodiment, cellulose nanofibers are produced according to methods known in the art in which cellulose is dissolved in a solvent and then electrospun. Suitable solvents can include N-methylmorphomine-N-oxide (NMMO), zinc chloride solutions, and the like. Particles can be present as a suspension or dispersion in the solution being used to make the fibers and combined with the electrospun fibers during the formation process. Alternatively, a particle-forming precursor can be present, or the particles can be added as a dry powder or entrained in a mist or spray as nanofibers are being produced. Charge on the particles or the entraining droplets can be added to enhance delivery of the particles to the electrospun web. Suitable particles can include silver (e.g., nanoparticles of silver), superabsorbent particles that can be entrained or entrapped in electrospun fibers (typically added external to electrospinning needles), minerals such as titanium dioxide or kaolin, odor control agents such as zeolites, sodium bicarbonate, or activated carbon particles, and the like.

In one embodiment protein nanofibers, such as fibrinogen fibers, elastin-mimetic fibers, etc., are combined with the coarse fibers. In one embodiment inorganic and hybrid (organic/inorganic) nanofibers are used. In one embodiment, polysaccharide nanofibers made from bacteria (e.g., bacterial cellulose) are used.

In another embodiment nanofibers known as splittable fibers are used, in which a fiber, such as a microfiber, is exposed to a swelling agent such as sodium hydroxide to cause it to split into numerous small filaments, or "islands-in-the-sea" fibers, in which a precursor fiber comprises multiple filaments (islands) in a removable matrix (sea) that typically is dissolved away. See, for example, http://www.ifj.com/issue/october98/story8.html. By way of example, islands-in-the-sea nanofibers can be polypropylene islands in a PVA sea, polyester islands in a polyethylene sea, and so forth. Fiber diameter can be from about 0.1 to about four (4) microns.

In one embodiment, fibers prepared by nanofabrication techniques such as printing, atomic force microscopy assembly, or any of the techniques known for producing the setae in gecko-like adhesives, as described in U.S. patent application Ser. No. 10/747,923, entitled "Gecko-like Fasteners for Disposable Articles," filed Dec. 29, 2003, are used.

Figure 5:
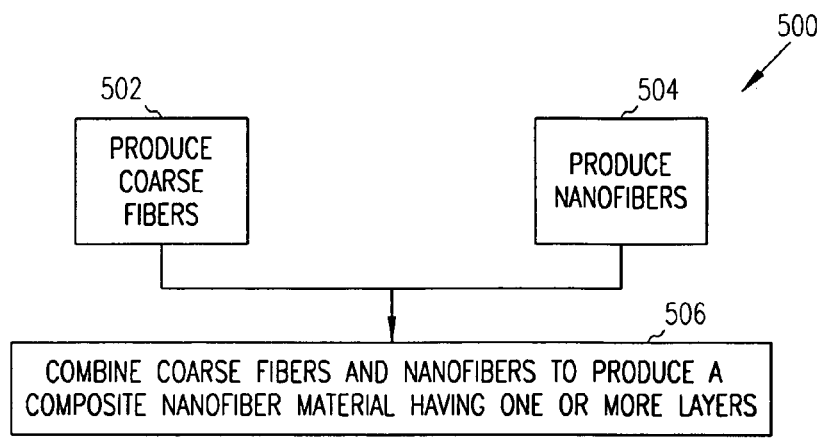
FIG. 5 is a block diagram showing a process for forming a composite electrospun material in accordance with one embodiment of the present invention.

FIG. 5 is a block diagram of a process 500 for forming a composite nanofiber material in one embodiment of the present invention. The process begins by producing 502 coarse fibers. The process further includes producing 504 nanofibers. The coarse fibers and nanofibers are then combined 506 to produce a composite nanofiber material having one or more layers. In one embodiment, the coarse fibers and nanofibers are combined on a moving substrate wherein the coarse fibers are present on the moving substrate prior to the nanofibers being added. In one embodiment the coarse fibers and nanofibers are deposited onto a moving substrate at about the same time. In one embodiment more than one type of coarse fiber is used. In one embodiment there is additionally or alternatively more than one type of nanofiber. In one embodiment one or more types of nanofibers are applied sequentially to the moving substrate. In one embodiment one or more types of nanofibers are applied substantially simultaneously to the moving substrate. In one embodiment a non-gradient composite nanofiber material is formed. In one embodiment a gradient composite nanofiber material is formed. The gradient composite nanofiber material can have a gradient in the thickness direction, in the plane of the material or both. In one embodiment, the coarse fibers are selected from the group consisting of meltblown (MB) fibers, spunbonded fibers, paper-making fibers, pulp fibers, fluff, cellulose fibers, nylon staple fibers, and the like, including any combinations thereof. In one embodiment, the nanofibers are electrospun fibers formed by any suitable method, including with the use of a needle and/or slot.

Composite nanofiber webs produced by the methods described herein can have varying properties depending on a number of parameters such as the percentage of nanofibers, the type of nanofibers, presence of ions in the gas or melt phases, all of the other process variables noted herein, and so forth. In one embodiment the composite nanofiber webs are gradient composite webs and/or non-gradient composite webs having a high porosity (e.g., at least about 20%) with relatively low pore sizes (e.g., less than about 5 microns. Such features are important in several types of absorbent products, filters of many kinds, medical goods, and so forth. In one embodiment, the porosity of a composite electrospun material is about 10 to about 95%, such as from about 50 to about 90%, or from about 30 to about 80%. In one embodiment, the pore size as measured by mercury porosimetry is from about 0.1 to about 10 microns, such as from about 0.5 to about 3 microns, or from about 0.1 to about 2 microns, or from about 0.2 to about 1.5 microns, or less than about 1 micron.

The use of composite nanofiber materials in various products is discussed in more detail below, but, generally speaking, the materials of the present invention are useful in a wide variety of products, including absorbent articles such as diapers, training pants, feminine napkins, adult incontinence garments, and the like. In one embodiment, the materials are used as distribution materials to hold and/or move liquid. In one embodiment, materials which are both hydrophobic and porous, e.g., a meltblown/electrospun fiber composite, can not only be used as an absorbent material to help keep the skin dry, but can also be used as a covering which allows fluid to pass through. In one embodiment, the composite nanofiber materials described herein are used in a non-absorbent article (e.g., gloves) or on a non-absorbent side of an absorbent article, e.g., an outer cover layer.

Such materials are useful for virtually any type of protective clothing, including any type of disposable garment, such as garments requiring varying surface properties, barrier clothing, and the like. For example, the composite nanofiber materials described herein can be incorporated into any type of disposable garment including, but not limited to, hospital garments such as surgical gowns, hair or head coverings (e.g., shower caps, hairnets, surgical caps, etc.), shoe covers, disposable patient gowns, laboratory coats, face masks, surgical gloves (e.g., for wicking moisture away from the hand and/or improving barrier functions), other medical and surgical goods including, but not limited to, sterile wrap, wound covers, hemostatic articles, and so forth. Specifically, the composite nanofiber materials of the present invention can help prevent fluids, such as bodily fluids, from penetrating the material and contacting the user. In one embodiment, the barrier is a breathable barrier, as is known in the art. In one embodiment, the composite nanofiber material includes hydrophobic fibers for use as a breathable barrier. It should be noted that the materials are useful as breathable materials for any purpose, including, but not limited to gloves, liners (e.g., exterior or interior lining of a glove), barrier layers, outer covers, absorbent core linings, barrier tissue, cuffs, wings, waistbands, and the like, found in absorbent articles. Such materials are also useful in wipes (including two-sided wipes or wipes with gradients in surface chemistry or other properties), face masks, air filters, water filters, sterile wrap, and so forth.

The high surface area of the various composite nanofiber materials described herein additionally allows such materials to be useful in filtration applications, such as to absorb odors, particles, and so forth. In one embodiment, the materials described herein are used in a high efficiency filtration device for water or air. In one embodiment the materials described herein are combined with conventional filtration materials, such as activated charcoal, and the like.

In one embodiment, composite nanofiber materials having gradients in one or more directions as described herein are used in absorbent articles in the intake region to provide varying properties within a single material or web. For example, wicking properties provided by these materials provide fluid flow control, barrier properties, and so forth. Therefore, it is possible for one region to be hydrophobic, which aids in wicking moisture away from the skin, and another area to be hydrophilic, and therefore located away from the fluid target area.

In one embodiment one or more of the composite nanofiber materials of the present invention are laminated to another layer known to provide strength, (e.g., such as a meltblown web, a polyolefin film or other film layer, an apertured film, a scrim layer, a tissue layer such as a cellulosic web having a basis weight of about 20 grams per square meter or greater, a woven layer, and the like). In this way, a sufficiently strong laminate is provided which is also capable of controlling surface properties (e.g., water deflection, etc.)

Portions of various garments or entire garments (for infants, children or adults), can be made using any of the composite nanofiber materials described herein. In one embodiment, the materials made from the processes described herein are useful as an insert, which can be comprised of a fluid impervious backing sheet or outer cover, fluid pervious facing sheet or liner, absorbent core and an intake/distribution or surge layer.

In one embodiment, the outer cover serves as a fluid barrier and can be made from any suitable liquid impermeable material or a material treated to be liquid impermeable, including any of the composite nanofiber materials described herein. In one embodiment, the outer cover is a laminate comprised of an inner liner layer and an outer film layer, such as a polyethylene film. In one embodiment, "Breathable stretch thermal laminate" (BSTL) is used for the outer cover. In an alternative embodiment the outer cover is an opaque sheet of material with an embossed or matte surface that is about one mil thick, although the invention is not so limited. In another alternative embodiment, the outer surface is made of extensible materials, such as necked, pleated (or micropleated) or creped nonwovens, including spunbond polypropylenes, bonded carded webs, or laminates of nonwovens and films, including composite nanofiber materials, which are necked, pleated or creped so as to allow the outer cover to extend with minimal force, further including any type of composite nanofiber material as described herein. For example, a suitable extensible material is a 60% necked, polypropylene spunbond having a basis weight of about 1.2 osy. In one embodiment, the polypropylene spunbond fibers are combined with one or more types of electrospun fibers. The cover sheet and outer cover can also be made of nonwovens, films, or composites of films and nonwovens or composite nanofiber materials. For a further description of extensible materials, see U.S. patent application Ser. No. 09/855,182, filed on May 14, 2001, entitled, "Absorbent Garment with Expandable Absorbent Element," commonly assigned, and hereby incorporated herein by reference.

The liner serves as a fluid barrier and can be made from any suitable material or materials, including the composite nanofiber materials described herein. In one embodiment, the liner is made from any soft, flexible porous sheet that permits the passage of fluids therethrough, including, but not limited to, hydrophobic or hydrophilic nonwoven webs, wet strength papers, spunwoven filament sheets, and so forth, further including composite nanofiber materials. In one embodiment, the inner bodyside surface is made from spunwoven polypropylene filaments or a composite nanofiber material with spot embossing, further including a perforated surface or suitable surfactant treatment to aid fluid transfer. In one embodiment, the liner is a laminate comprised of an inner liner layer, which, in one embodiment, is made from the composite nanofiber materials described herein, and an outer film layer, such as a polyethylene film. In one embodiment, "breathable stretch thermal laminate" (BTSL) is used for the liner.

The absorbent core or absorbent batt located between the outer cover and liner serves to absorb liquids, as is known in the art, and can be made from any suitable material, including any of the composite nanofiber materials described herein. The absorbent batt can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. In certain embodiments, different types of superabsorbent material may be used among the different types of products, such as diapers. The delivery of different superabsorbent materials may be achieved using a pulsed superabsorbent delivery system. For example, the absorbent structure in one type of diaper may include a superabsorbent material that provides adequate performance for many general-use situations but fails to deliver optimum performance under some use conditions. Suitable superabsorbent materials can be selected from natural, synthetic, and modified natural polymers and materials. The superabsorbent materials can be inorganic materials, such as silica gels, or organic compounds, such as crosslinked polymers. In one embodiment the superabsorbent is any type of composite electrospun material as described herein. The fibers can be fluff pulp materials or any combination of crosslinked pulps, hardwood, softwood, and synthetic fibers and electrospun fibers or other types of nanofibers. Suitable superabsorbent materials are available from various commercial vendors, such as Dow Chemical Company located in Midland, Mich., U.S.A., BASF, located in Portsmouth, Va., U.S.A., and Degussa, located in Greensboro, N.C., U.S.A. Typically, a superabsorbent material is capable of absorbing at least about 15 times its weight in water, and desirably is capable of absorbing more than about 25 times its weight in water.

Airlaid and wetlaid structures typically include binding agents, which are used to stabilize the structure. Other absorbent materials, alone or in combination, and including webs of carded or air-laid textile fibers, multiple plys of creped cellulose wadding, various super absorbent materials, various foams, such as synthetic foam sheets, absorbent films, and the like can also be used. The batt can also be slightly compressed or embossed in selected areas as desired. Various acceptable absorbent materials are disclosed in U.S. Pat. No. 5,147,343, entitled, "Absorbent Products Containing Hydrogels With Ability To Swell Against Pressure," U.S. Pat. No. 5,601,542, entitled "Absorbent Composite," and U.S. Pat. No. 5,651,862, entitled, "Wet Formed Absorbent Composite," all of which are commonly assigned and hereby incorporated herein by reference. Furthermore, the proportions of high-absorbency particles can range from about zero (0) to about 100%, and the proportion of fibrous material from about zero (0) to about 100%.

In one embodiment, the absorbent batt is a folded absorbent material made of fibrous absorbent materials with relatively high internal integrity, including for example one made with thermoplastic binder fibers in airlaid absorbents, e.g., pulp, bicomponent binding fibers, and superabsorbents, which have higher densities in the folded regions, further including any type of composite nanofiber materials as described herein. In one embodiment, composite electrospun materials are used. The higher density and resulting smaller capillary size in these regions promotes better wicking of the liquid. Better wicking, in turn, promotes higher utilization of the absorbent material and tends to result in more uniform swelling throughout the absorbent material as it absorbs the liquid. The intake/distribution layer is made from any suitable material to increase the weight of fluid intake retention.

The surge layer is made from any suitable material, including any of the composite nanofiber materials described herein, and is designed to increase the weight of fluid intake retention.

Other details of conventional construction and materials of disposable garments are understood in the art and will not be discussed in detail herein. See, for example, U.S. Pat. No. 4,437,860 to Sigl, commonly assigned, which is hereby incorporated herein by reference.

Figure 6:
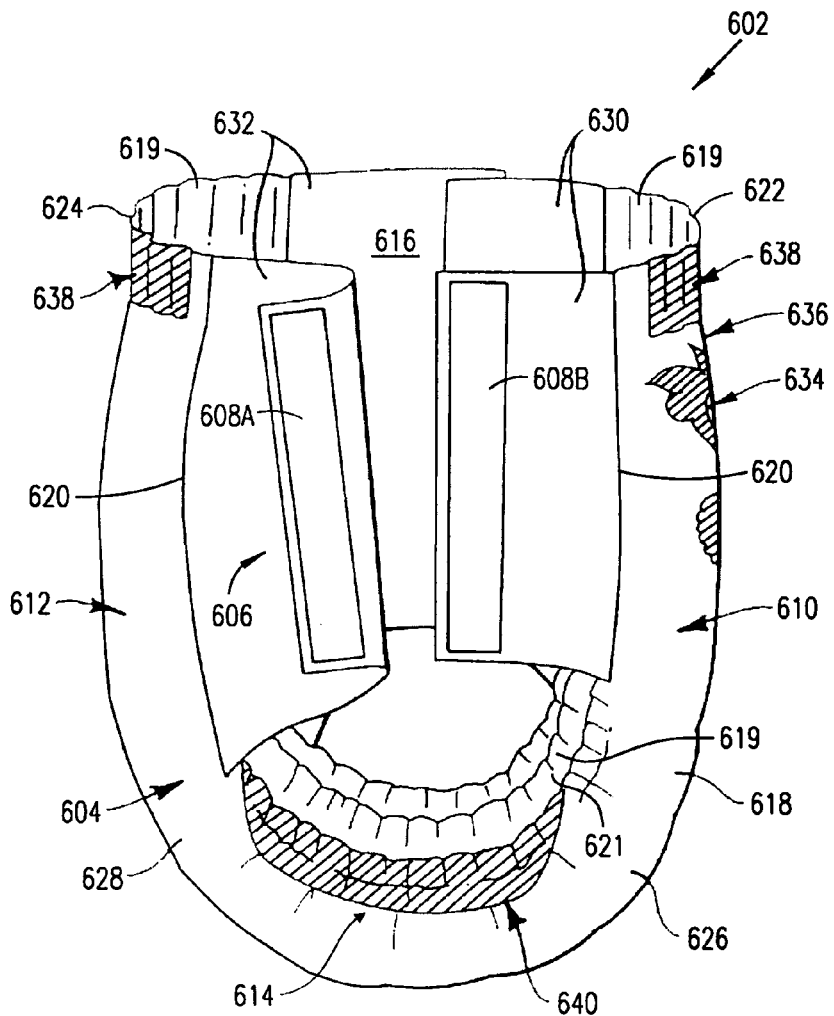
FIG. 6 is a schematic illustration of an exemplary product containing a composite electrospun material in accordance with one embodiment of the present invention.

In one embodiment, the composite nanofiber materials, such as composite electrospun materials, produced according to the methods described herein are used in an absorbent article 602 as shown in FIG. 6. In one embodiment the absorbent article 602 is a diaper. In another embodiment, the absorbent article 602 is a training pant, such as the training pant described in U.S. Pat. No. 6,562,167, issued to Coenen et al., and hereby incorporated herein by reference.

The absorbent article 602 comprises an absorbent chassis 604 and a fastening system 606 having a pair of fasteners, 608A and 608B to secure front and rear portions of the absorbent chassis 604 together. The fasteners 608A and 608B can be adhesive strips, mechanical fasteners, and the like. The absorbent chassis 604 defines a front waist region 610, a back waist region 612, a crotch region 614 interconnecting the front and back waist regions 610 and 612, respectively, an inner surface 616 which is configured to contact the wearer, and an outer surface 618 opposite the inner surface 616 which is configured to contact the wearer's clothing. In most embodiments, elastic 619 is present in the front waist region 610, the back waist region 612 and the crotch region 614 as shown. The crotch region 614 further includes containment flaps 621 as shown. Any of the components in the chassis 604 can include nanofibers, such as the composite electrospun materials described herein. The absorbent chassis 604 also defines a pair of transversely opposed side edges 620 and a pair of longitudinally opposed waist edges, which are designated front waist edge 622 and back waist edge 624. The front waist region 610 is contiguous with the front waist edge 622, and the back waist region 612 is contiguous with the back waist edge 624.

The absorbent article further comprises an outer cover 626. In general, the outer cover 626 can comprise one or more layers of nanofibers on the outward facing surface. In one embodiment, the nanofibers are hydrophobic. The illustrated absorbent chassis 604 comprises a structure 628 which can be rectangular or any other desired shape, a pair of transversely opposed front side panels 630, and a pair of transversely opposed back side panels 632. The structure 628 and front and back side panels, 630 and 632, respectively, can comprise two or more separate elements, as shown in FIG. 6, or can be integrally formed. Integrally formed front and back side panels 630 and 632, respectively, and composite structure 628 would comprise at least some common materials, such as the bodyside liner, flap component, outer cover, other materials and/or combinations thereof, and could define a one-piece elastic, stretchable, or nonstretchable absorbent article 602, which can further comprise segments of foam layers (not shown) disposed on the outer surface thereof.

The absorbent article 602, and, in particular, the outer cover 626 can comprise one or more appearance-related components such as printed graphics 634 on the front surface 636, a colored stretchable waist band 638, and so forth. Examples of appearance-related components include, but are not limited to: graphics; highlighting or emphasizing leg and waist openings in order to make product shaping more evident or visible to the user (e.g., a printed leg opening region 640); highlighting or emphasizing areas of the absorbent article 602 to simulate functional components such as elastic leg bands, elastic waistbands, simulated "fly openings" for boys, ruffles for girls; highlighting areas of the absorbent article 602 to change the appearance of the size of the absorbent article 602; registering wetness indicators, temperature indicators, and the like in the absorbent article 602; registering a back label, or a front label, in the absorbent article 602; and, registering written instructions at a desired location in the absorbent article 602.

The invention will be further described by reference to the following examples, which are offered to further illustrate various embodiments of the present invention. It should be understood, however, that many variations and modifications may be made while remaining within the scope of the present invention.

Example 1

Making Electrospun Nanofiber Composites with Nonwoven and Paper Fibers

Materials and Preparation

Polyethylene Oxide (PEO) with a molecular weight (MW) of 100,000, Catalog No. 18, 198-6, from Sigma-Aldrich, having offices in Saint Louis, Mo., was used for the electrospun fibers. Additionally, thermoplastic adhesive polymer H2025a from Findley Adhesive Company, a division of Bostik Findley, having offices in Wauwatosa, Wis., was used as the meltblown fibers. Softwood fluffing CR-1654 was obtained from US Alliance Pulp Mills, having offices in Coosa, Ala., was used for the fluff fibers.

A 15% PEO solution was prepared in ultra-filtered grade, distilled, deionized water having a resistivity reading of 18 MΩ.cm. With the aid of a Model '22' Syringe Pump from Harvard Apparatus, Inc., having offices in Holliston, Mass., the solution was extruded at ambient temperature and pressure at a flow rate of approximately 100 uL/ml from a one (1) mL syringe through Tygon® brand tubing (1.6 mm id) to a positively charged metal blunt-tipped needle (22 G×3.8 cm (1.5) in) made by Becton-Dickson & Co., having offices in Franklin Lakes, N.J. A High Voltage Supply ES30P/DDPD (having a low current power supply) from Gamma High Voltage Research, Inc., having offices in Ormand Beach, Fla., was utilized to establish the 18 kV electric potential gradient. PEO fibers were electrospun and intertwined with meltblown or fluff fibers and the formed composite was collected on a grounded aluminum plate located a distance of approximately 15 cm below the tip of the needle.

The temperature was set to approximately 350° C. in a PAM 600 Spray Melt Gun from Fastening Technology, Inc., having offices in Charlotte, N.C., to heat and melt adhesive polymer H2025a. Gun air pressure was adjusted to approximately 4.2 kg/cm$^2$ (about 60 lb/in$^2$) to cause the melted polymer to form a spray. The spray gun was aimed at the sample collector, i.e., the aluminum plate, beside the electrospun device, and activated. The spray stream formed by the melted adhesive polymer intertwined with the electrospun PEO fiber. Samples were collected at the grounded aluminum plate. In a control test, the thermoplastic adhesive polymer H2025 sample was collected under the same conditions without being intertwined with PEO nanofibers. The resulting material had a thickness of about 50 to about 100 microns.

Scanning Electron Microscope Images

SEM images were taken using S4500 Field Emission SEM, which operated at an accelerating voltage of 5 kV. An upper detector was used (pure SEI) at a working distance of about nine (9) mm. The samples were coated with approximately 20 nm chromium, and the images were taken at magnifications ranging from 250 to 15,000×.

Figure 7:
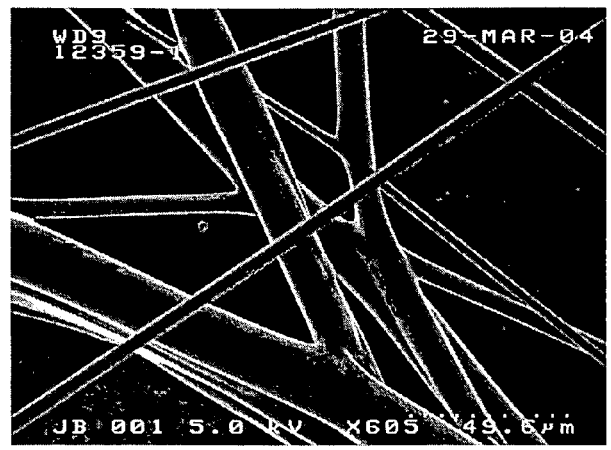
FIG. 7 is a SEM micrograph of a meltblown (MB) adhesive polymer fiber with smooth surface morphology at a magnification of 605×.

FIG. 7 is a SEM micrograph of a MB adhesive polymer fiber approximately 2.5 to 20 microns in diameter with smooth surface morphology at a magnification of 605×.

Figure 8:
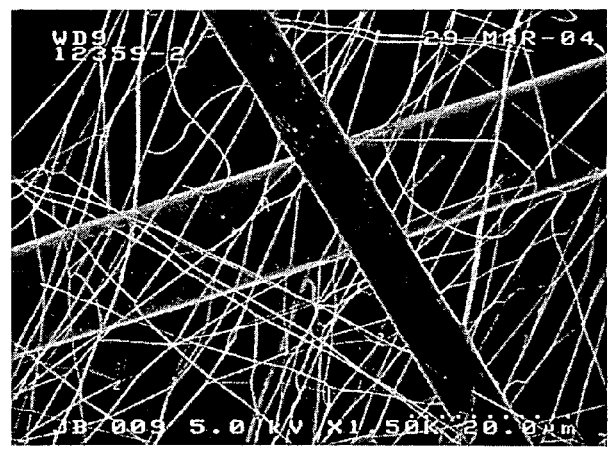
FIG. 8 is a SEM micrograph of an intertwined polyethylene oxide (PEO) nanofiber/MB composite morphology at a magnification of 1500× in accordance with one embodiment of the present invention.

FIG. 8 is a SEM micrograph of an intertwined polyethylene oxide (PEO) nanofiber/meltblown (MB) composite morphology at a magnification of 1500×. PEO electrospun nanofiber ranges from about 100 to 300 nm, while meltblown adhesive polymer fiber ranging from about 800 nm to 10 microns.

Figure 9:
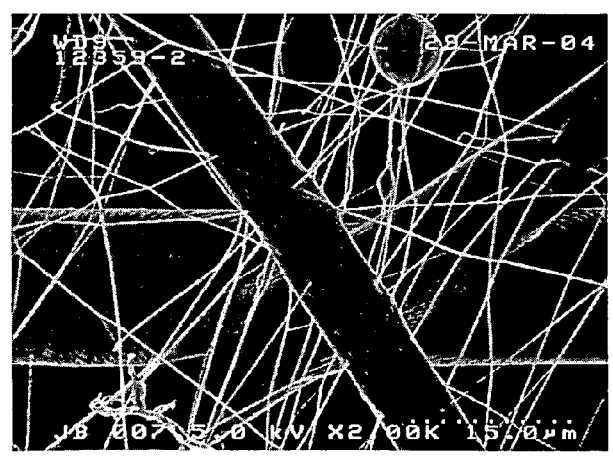
FIG. 9 is a SEM micrograph of the intertwined PEO nanofiber/MB composite morphology of FIG. 8 in a different sample area at a magnification of 2000× in accordance with one embodiment of the present invention.

FIG. 9 is a SEM micrograph of the intertwined PEO nanofiber/MB composite morphology of FIG. 8 in a different sample area at a magnification of 2000×. PEO electrospun nanofiber size ranges from about 100 to 300 nm, while meltblown adhesive polymer fiber size ranging from about 800 nm to 15 microns. A very small percent of bead morphology is also observed in the PEO nanofiber network.

Figure 10:
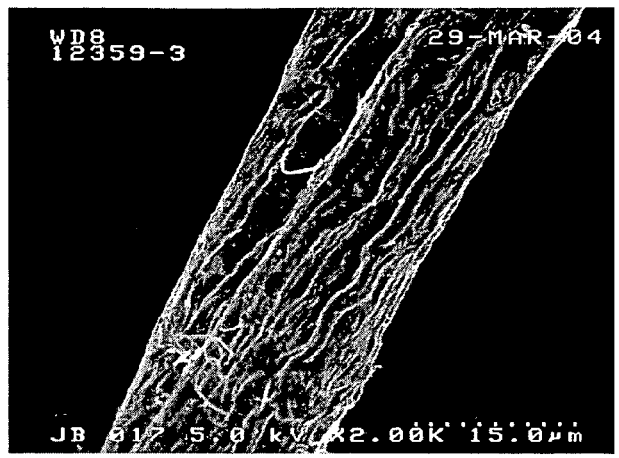
FIG. 10 is a scanning electron microscope (SEM) micrograph of cellulose fibers with rough surface morphology at a magnification of 2000×.

FIG. 10 is a scanning electron microscope (SEM) micrograph of cellulose fibers approximately 20 microns in diameter with rough surface morphology at a magnification of 2000×.

Figure 11:
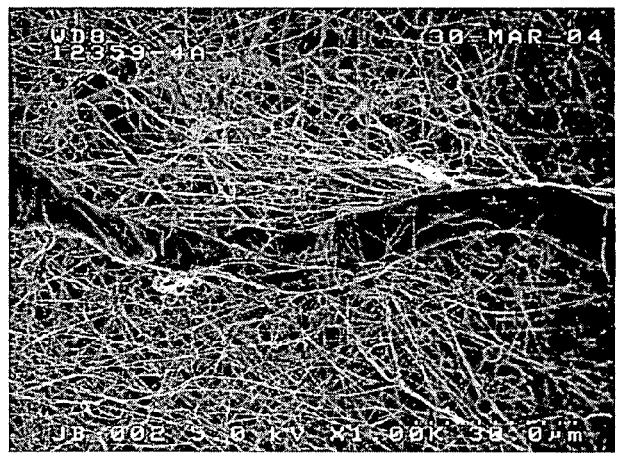
FIGS. 11 and 12 are SEM micrographs of intertwined PEO nanofiber/cellulose fluff composite morphologies at a magnification of 1000× and 2000×, respectively, in accordance with embodiments of the present invention.
Figure 12:
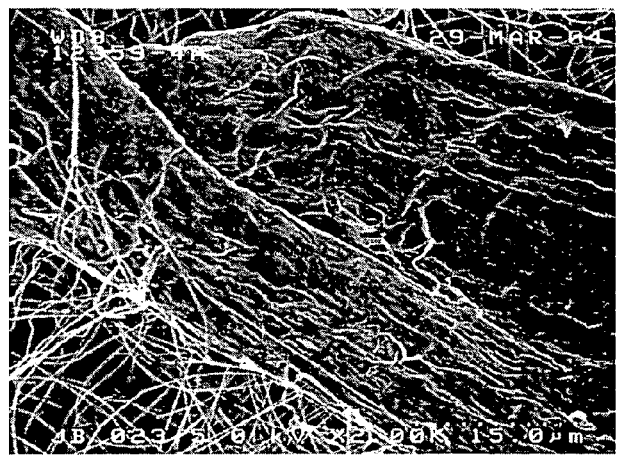

FIGS. 11 and 12 are SEM micrographs of intertwined PEO nanofiber/cellulose fluff composite morphologies at a magnification of 1000× and 2000×, respectively. PEO electrospun nanofibers were intertwined with the airblown fluff as described earlier and formed the composite. PEO nanofiber ranges from about 100 to 300 nm, while large cellulose fibers range from about 20 to 25 microns. (Note the difference in appearance between FIG. 11 and FIG. 10 as the electrospun fibers are the majority component in FIG. 11 and the fibers are now intertwined with the airblown cellulose fibers).

Figure 13:
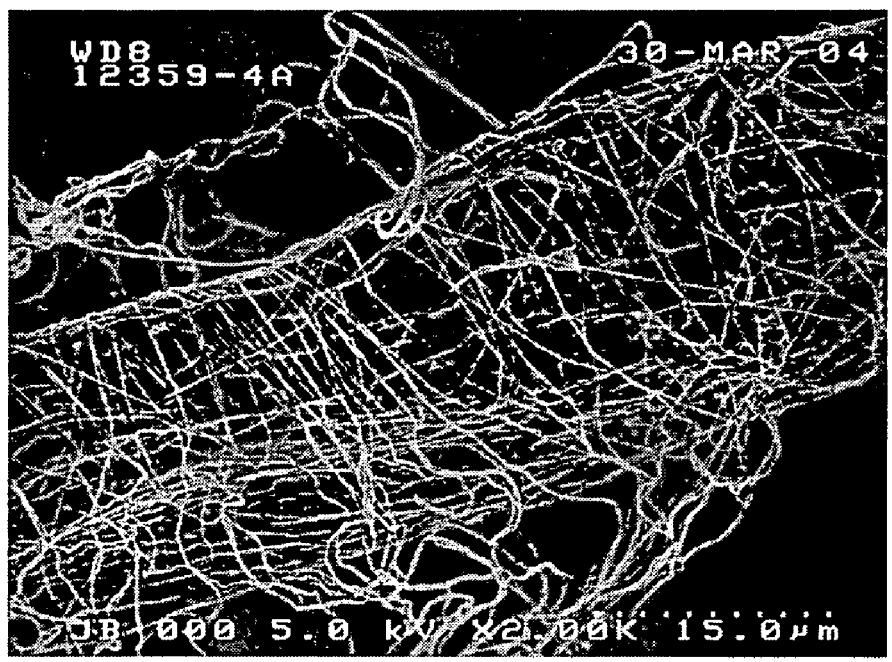
FIGS. 13 and 14 are SEM micrographs of intertwined PEO nanofiber/cellulose fluff composite morphologies at a magnification of 2000× and 4000×, respectively, in accordance with embodiments of the present invention.
Figure 14:
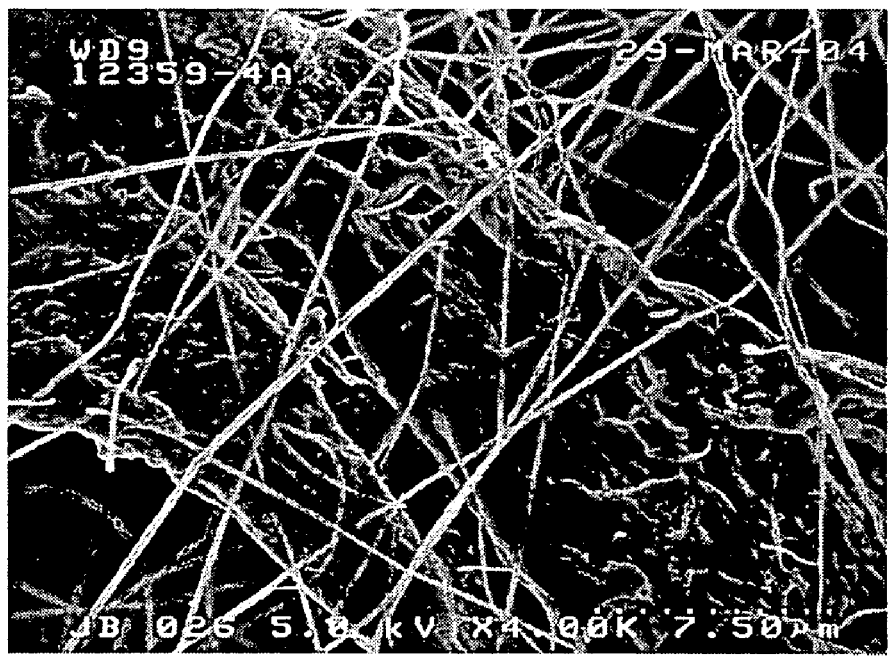

FIGS. 13 and 14 are SEM micrographs of intertwined PEO nanofiber/cellulose fluff composite morphologies at a magnification of 2000× and 4000×, respectively. Nano-sized PEO electrospun fibers (100 to 300 nm) were observed to wrap around single cellulose fiber of a big fiber size (approximately 20 microns in diameter) in the intertwined composite made by described process. PEO nanofiber ranges from about 100 to 300 nm, while large cellulose fibers range from about 20 to 25 micron. (Note the difference in appearance between FIG. 13 and FIG. 10 as FIG. 13 shows the single airblown cellulose fiber (majority component) wrapped by an electrospun nanofiber).

Example 2

Materials and Preparation

Polyethylene Oxide (PEO) with a molecular weight (MW) of 900,000, Catalog No. 18, 945-6, from Sigma-Aldrich, was used. Additionally, approximately 17 g/m$^2$ (gsm) of wetlaid nonwoven material, i.e., a cellulose-polymer material, containing approximately 70% softwood and abaca (hemp) fiber and about 30% polyester staple fiber was used. The wetlaid material was made by Dexter Nonwoven Materials, having offices in Windsor Locks, Conn., using conventional wetlaid nonwoven manufacturing processes known in the art. As part of this process, a sheet of the material was saturated with a synthetic acrylic binder, which comprises about 30%, by weight, of the total material. Two 2×2 cm samples were prepared and each tested three times (See Table 1).

A portion of the procedure as described in Example 1 above was then followed. However, in this instance, a 2% PEO solution was prepared in ultra-filtered grade, distilled, deionized water (18 MΩ.cm). With the aid of a Model '22' Syringe Pump from Harvard Apparatus, Inc., the solution was again extruded at ambient temperature and pressure at a flow rate of approximately 100 uL/ml through a positively charged metal blunt-tipped needle (22 G×3.8 cm (1.5 in)). A High Voltage Supply ES30P/DDPD (having a low current power supply) from Gamma High Voltage Research, Inc. was utilized to establish the 18 KV electric potential gradient. The needle was connected to a one (1) ml syringe using Tygon® tubing having a 1.6 mm inner diameter.

However, rather than being intertwined with meltblown or fluff fibers as described in Example 1 above, the resulting PEO nanofibers were electropsun and then collected on one side of the wetlaid material to form a nanofiber wetlaid composite. Specifically, one of the previously prepared wetlaid sample was laid on top of a grounded aluminum plate located a distance of approximately 15 cm below the tip of the needle. PEO nanofibers were then collected on top to produce a nanofiber wetlaid composite material. (The other wetlaid sample remained untreated and was used as a control). The PEO nanofiber coating added about five (5) % additional weight to the wetlaid material. The coating thickness is comparable to the type of thickness achieved with the intertwined examples of Example 1, namely, about 50 to about 100 microns. For purposes of this experiment, it was assumed that the material prepared in this experiment is comparable to the intertwined material prepared in Example 1.

Air Permeability (Porosity) Test

The air permeability tests were conducted according to the ASTM D 737-75 (1980) Standard Test Method for Air Permeability of Textile Fabrics. The instrument used in this test was an air permeability tester Model No. TEXTEST FX 3300 from TexTest Ag., having offices in Zurich, Switzerland. This test measures the rate and volume of air flow through a fabric under a prescribed surface pressure differential. The higher the result reading, the more open the material is, thus allowing more air to pass through. Air flow rate and volume are an indication of fabric breathability.

Under controlled conditions, a suction fan draws air through a known area of fabric approximately 38 cm$^2$ (5.9 in$^2$). The air flow through the test specimen is measured with a variable orifice. The air permeability of the test specimen is determined from the pressure drop across this orifice, and is digitally displayed in the selected unit of measure for direct reading. The rate is adjusted to a prescribed pressure differential, in this instance approximately 0.02 lb/in$^2$ (about 125 Pa).

Results

The nanofiber wetlaid composite material sample was then tested (three times) for air permeability and compared with the untreated wetlaid nonwoven sample (also tested three times). Each sample was about 5.1 by 5.1 cm (about two (2) by two) in). Results are shown in Table 1 below and expressed as air flow:

TABLE 1

Air Permeability Results for Untreated and Treated Wetlaid Composite Material

|  | Air flow m$^3$/min (ft$^3$/min.) | Average air flow m$^3$/min (ft$^3$/min) |
|---|---|---|
| Untreated Wetlaid | 9.6 (338) | 9.5 (337) |
|  | 9.7 (343) |  |
|  | 9.4 (331) |  |
| Nanofiber Wetlaid Composite | 9.1 (322) | 9 (318) |
|  | 8.9 (314) |  |
|  | 9 (318) |  |

The electrospun PEO nanofiber coating on the conventional wetlaid material had a very small effect (6%) on air permeability drop (about nine (9) m3/min) when compared with untreated wetlaid material (about 9.5 m3/min). This result indicates that the electrospun materials have minimal impact on the porosity of conventional materials, yet have the advantages as described herein.

CONCLUSION

In some of the embodiments described herein, mixtures of various nanofibers are created by using multiple discharge tubes containing different polymers, each of which produce nanofibers which are deposited on a collection grid and intermingled with and/or layered with coarse fibers or a combination of coarse fibers and nanofibers. Thus, for example, mixtures of hydrophobic and hydrophilic nanofibers can be created, such as composites of polylactides or polyactic acid polymers, spun out of a solution and coupled with polyolefin coarse fibers, such as polyethylene, spun from a melt, or with Kraton®, a polymer made by Kraton Polymers, having offices in Houston, Tex., or other fibers electrospun from a solution with a suitable solvent. The resulting composite nanofiber materials provide webs useful in disposable absorbent articles. Such webs can be part of intake layers, protective covers, distribution materials, and outer covers of articles as described herein.

Embodiments of the present invention provide significant advantages over other fibrous products and methods for manufacture thereof. Nanofibers produced by electrospinning or other methods can produce materials having very large surface areas for a given weight. When these nanofibers are combined with conventional nonwovens having larger fiber sizes, as described herein, the resulting composite materials can maintain similar porosity properties while providing a relatively low pore size and high surface area.

All publications, patents, and patent documents cited in the specification are incorporated by reference herein, each in their entirety, as though individually incorporated by reference. In the case of any inconsistencies, the present disclosure, including any definitions therein, will prevail.

Although specific aspects have been illustrated and described herein, it will be appreciated by those of ordinary skill in the art that any arrangement that is calculated to achieve the same purpose may be substituted for the specific aspect shown. For example, although the invention has been described primarily in terms of electrospun fibers, it is to be understood that nanofibers of any type can be used. This application is intended to cover any adaptations or variations of the present invention. Therefore, it is manifestly intended that this invention be limited only by the claims and the equivalents thereof.

What is claimed is:

1. A composite material comprising:
   a plurality of electrospun fibers intertwined with a plurality of coarse fibers to form a single layer, wherein the plurality of electrospun fibers and the plurality of coarse fibers are distributed non-uniformly in the planar direction within the single layer to form one or more gradients, the distribution of coarse fibers and electrospun fibers being consistent in the z-direction of the single layer.

2. The composite material of claim 1 wherein the plurality of electrospun fibers have an electrospun fiber average diameter and the plurality of coarse fibers have a coarse fiber average diameter, wherein a ratio of the coarse fiber average diameter to the electrospun fiber average diameter is about 5 or more.

3. The composite material of claim 1 wherein the composite material comprises about one (1) to 99% content, by weight, of electrospun fiber.

4. The composite material of claim 1 wherein at least a portion of the plurality of the coarse fibers are microfibers.

5. The composite material of claim 1 wherein the plurality of coarse fibers are made from at least two different types of coarse fibers.

6. The composite material of claim 1 wherein the plurality of coarse fibers are selected from the group consisting of meltblown (MB) fibers, spun-bonded fibers, paper-making fibers, pulp fibers, fluff, cellulose fibers, nylon staple fibers, and any combinations thereof.

7. The composite material of claim 6 wherein the coarse fibers form a meltspun web.

8. The composite material of claim 7 wherein the meltspun web is made from meltblown fibers.

9. The composite material of claim 7 wherein the meltspun web is made from spunbond fibers.

10. The composite material of claim 1 wherein the coarse fibers are loosely combined with a spunbond web.

11. The composite material of claim 1 wherein the at least one of the one or more gradients is a planar gradient.

12. The composite material of claim 11 wherein at least one of the one or more planar gradients is a surface chemistry gradient.

13. The composite material of claim 1 wherein the plurality of electrospun fibers are produced from at least two different polymers or polymer blends.

14. The composite material of claim 13 wherein the plurality of electrospun fibers are produced from three different polymers or polymer blends.

15. The composite material of claim 13 wherein the at least two different polymers or polymer blends are selected from the group consisting of a polylactide, polylactic acid, polyolefin, polyacrylonitrile, polyurethane, polycarbonate, polycaprolactone, polyvinyl alcohol (PVA), cellulose, silk fibroin, polyaniline, polystyrene, polyethylene oxide, polyacrylonitrile-acrylamide, N,N-dimethylformamide, chitosan nylon, polyvinyl alcohol, chitosan nylon, polystyrene, protein, and combinations thereof.

16. The composite material of claim 15 wherein the chitosan nylon is selected from the group consisting of Nylon 6, Nylon 406, Nylon 6-6 and combinations thereof.

17. The composite material of claim 13 wherein the at least two different polymers or polymer blends are each in a solvent selected from the group consisting of sulfuric acid, formic acid, chloroform, tetrahydrofuran, dimethylformamide, water, acetone, and combinations thereof.

18. The composite material of claim 1 wherein the plurality of electrospun fibers are made by at least two different methods.

19. The composite material of claim 1 wherein at least some of the plurality of electrospun fibers are selected from the group consisting of hydrophobic fibers, hydrophilic fibers and combinations thereof.

20. The composite material of claim 19 wherein the hydrophobic fibers are self-cleaning.

21. The composite material of claim 1 wherein the composite material has an air permeability drop no greater than about six (6) % less than the plurality of coarse fibers.

22. The composite material of claim 1 wherein the composite material has a porosity of at least about 20%.

23. The composite material of claim 1 wherein the composite material has a pore size of less than about 6 microns.

24. The composite material of claim 1 wherein one or more conductive polymers are contained in the single layer.

25. A composite material comprising:
   a plurality of electrospun fibers combined with a plurality of coarse fibers to form a plurality of layers, wherein the plurality of electrospun fibers and the plurality of coarse fibers are distributed non-uniformly within one or more of the plurality of layers to form one or more planar gradients, the distribution of coarse fibers and electrospun fibers being consistent in the z-direction of each layer.

26. The composite material of claim 25 wherein the plurality of electrospun fibers and the plurality of coarse fibers are also distributed non-uniformly between each of the plurality of layers to form one or more thickness gradients.

27. The composite material of claim 26 wherein at least one of the one or more gradients is a surface chemistry gradient.

28. The composite material of claim 25 wherein the plurality of electrospun fibers have an electrospun fiber average diameter and the plurality of coarse fibers have a coarse fiber average diameter, wherein a ratio of the coarse fiber average diameter to the electrospun fiber average diameter is about 5 or more.

29. The composite material of claim 25 wherein the composite material comprises about one (1) to 99% content, by weight, of electrospun fiber.

30. The composite material of claim 25 wherein at least a portion of the plurality of the coarse fibers are microfibers.

31. The composite material of claim 25 wherein the plurality of coarse fibers are selected from the group consisting of meltblown (MB) fibers, spun-bonded fibers, paper-making fibers, pulp fibers, fluff, cellulose fibers, nylon staple fibers and any combinations thereof.

32. The composite material of claim 25 wherein the plurality of electrospun fibers are produced from at least two different polymers or polymer blends.

33. The composite material of claim 32 wherein the at least two different polymers or polymer blends are selected from the group consisting of a polylactide, polylactic acid, polyolefin, polyacrylonitrile, polyurethane, polycarbonate, polycaprolactone, polyvinyl alcohol (PVA), cellulose, silk fibroin, polyaniline, polystyrene, polyethylene oxide, polyacrylonitrile-acrylamide, N,N-dimethylformamide, chitosan nylon, polyvinyl alcohol, chitosan nylon, polystyrene, protein, and combinations thereof.

34. The composite material of claim 33 wherein the chitosan nylon is selected from the group consisting of Nylon 6, Nylon 406, Nylon 6-6 and combinations thereof.

35. The composite material of claim 32 wherein the at least two different polymers or polymer blends are each in a solvent selected from the group consisting of sulfuric acid, formic acid, chloroform, tetrahydrofuran, dimethylformamide, water, acetone, and combinations thereof.

36. The composite material of claim 25 wherein the plurality of electrospun fibers are made by at least two different methods.

37. The composite material of claim 25 wherein at least some of the plurality of electrospun fibers are selected from the group consisting of hydrophobic fibers, hydrophilic fibers and combinations thereof.

38. The composite material of claim 37 wherein the hydrophobic fibers are self-cleaning.

39. The composite material of claim 25 wherein the composite material has an air permeability drop no greater than about six (6) % less than the plurality of coarse fibers.

40. The composite material of claim 25 wherein the composite material has a porosity of at least about 20%.

41. The composite material of claim 25 wherein the composite material has a pore size of less than about 5 microns.

42. The composite material of claim 25 further comprising one or more conductive polymers.

43. A composite material comprising:
a plurality of solution-based electrospun fibers made from one or more polymers and combined with a plurality of coarse fibers to form one or more layers, wherein the plurality of electrospun fibers have an electrospun fiber average diameter and the plurality of coarse fibers have a coarse fiber average diameter, wherein a ratio of the coarse fiber average diameter to the electrospun fiber average diameter is about 5 or more, wherein the electrospun fibers and the coarse fibers are distributed non-uniformly within one or more of the layers to form one or more planar gradients, the distribution of coarse fibers and electrospun fibers being consistent through the z-direction of each layer.

44. The composite material of claim 43 wherein the one or more polymers are selected from the group consisting of a polylactide, polylactic acid, polyolefin, polyacrylonitrile, polyurethane, polycarbonate, polycaprolactone, polyvinyl alcohol (PVA), cellulose, silk fibroin, polyaniline, polystyrene, polyethylene oxide, polyacrylonitrile-acrylamide, N,N-dimethylformamide, chitosan nylon, polyvinyl alcohol, chitosan nylon, polystyrene, protein, and combinations thereof.

45. The composite material of claim 43 wherein the one or more polymers is polyethylene oxide.

46. The composite material of claim 43 wherein the composite material has an air permeability drop no greater than about six (6) % less than the plurality of coarse fibers.

47. The composite material of claim 43 wherein the composite material has a porosity of at least about 20%.

48. The composite material of claim 43 wherein the composite material has a pore size of less than about 5 microns.

49. A composite material comprising:
a plurality of continuous electrospun fibers made from one or more polymers and combined with a plurality of coarse fibers to form one or more layers, wherein the plurality of electrospun fibers have an electrospun fiber average diameter and the plurality of coarse fibers have a coarse fiber average diameter, wherein a ratio of the coarse fiber average diameter to the electrospun fiber average diameter is about 5 or more, and wherein electrospun fibers and the coarse fibers are distributed non-uniformly within the one or more layers to form one or more planar gradients, the distribution of coarse fibers and electrospun fibers being consistent through the z-direction of such layer.

50. The composite material of claim 49 wherein at least one of the one or more gradients is a planar gradient.

* * * * *